US008586358B2

(12) United States Patent
Russell et al.

(10) Patent No.: US 8,586,358 B2
(45) Date of Patent: *Nov. 19, 2013

(54) HLA HOMOZYGOUS CELLS

(75) Inventors: David W. Russell, Seattle, WA (US); Roli K. Hirata, Seattle, WA (US)

(73) Assignee: University of Washington, Seattle, WA (US)

( * ) Notice: Subject to any disclaimer, the term of this patent is extended or adjusted under 35 U.S.C. 154(b) by 4 days.

This patent is subject to a terminal disclaimer.

(21) Appl. No.: 13/333,010

(22) Filed: Dec. 21, 2011

(65) Prior Publication Data

US 2012/0093790 A1  Apr. 19, 2012

Related U.S. Application Data

(63) Continuation of application No. 12/044,471, filed on Mar. 7, 2008, now Pat. No. 8,105,831.

(60) Provisional application No. 60/905,966, filed on Mar. 9, 2007.

(51) Int. Cl.
*C12N 5/00* (2006.01)
*C12N 15/00* (2006.01)

(52) U.S. Cl.
USPC .............................. 435/366; 435/455; 435/456

(58) Field of Classification Search
None
See application file for complete search history.

(56) References Cited

U.S. PATENT DOCUMENTS

| 6,986,887 B2 | 1/2006 | Lawman et al. |
| 7,030,292 B2 | 4/2006 | Yan et al. |
| 2003/0027331 A1 | 2/2003 | Yan et al. |
| 2007/0141702 A1 | 6/2007 | Revazova et al. |

FOREIGN PATENT DOCUMENTS

WO  9848005  10/1998

OTHER PUBLICATIONS

Reali et al. Differentiation of human adult CD34+ stem cells into cells with a neural phenotype: Role of astrocytes. Experimental Neurology, 2006, vol. 197, pp. 399-4406.*
Nepom et al. Electrophoretic analysis of human HLA-DR antigens from HLA-DR4 homozygous cell lines: Correlation between Beta-chain diversity and HLA-D. Proced. Natl. Acad. Sci., 1983, vol. 80, pp. 6962-6966.
Tsai et al. Reconstruction of Damaged Corneas by Transplantation of Autologous Limbal Epithelial Cells. New Engl. J. Med., Jul. 13, 2000, vol. 343, pp. 93.
Jin et al. Creation of a mouse expressing defective human factor IX. Blood, 2004, vol. 104, pp. 1733-1739.
Lupton et al. Dominant Positive and Negative Selection Using a Hygromycin Phosphotransferase-Thymidine Kinase Fusion Gene. Molecular Cellular Biol., 1991, vol. 11, pp. 3374-3378.
Chamberlain et al., "Gene Targeting in Stem Cells From Individuals With Osteogenesis Imperfecta," with Supporting Online Material, Science 303:1198-1201 (2004).
Hirata et al., "Targeted Transgene Insertion Into Human Chromosomes by Adeno-Associated Virus Vectors," Nat. Biotechnol. 20(7):735-738 (2002).
Hirata and Russell, "Design and Packaging of Adeno-Associated Virus Gene Targeting Vectors," J. Virol. 74 (1 0):4612-4620 (2000).
Inoue et al., "Introduction of Single Base Substitutions at Homologous Chromosomal Sequences by Adeno-Associated Virus Vectors," Mol. Ther. 3(4):526-530 (2001).
Inoue et al., "High-Fidelity Correction of Mutations at Multiple Chromosomal Positions by Adeno-Associated Virus Vectors," J. Virol. 73(9):7376-7380 (1999).
Russell and Hirata, "Human Gene Targeting by Viral Vectors," Nat. Genet. 18:325-330 (1998).
Harvard Medical School, "Homozygous MHC-matched mouse ES cells isolated", BioCentury Publications, Dec. 15, 2006.
Kim K. et al. "Histocompatible Embryonic Stem Cells by Parthenogenesis" and Supporting Material, Science 315, 482 (2007).

* cited by examiner

*Primary Examiner* — Deborah Crouch
(74) *Attorney, Agent, or Firm* — Mark J. FitzGerald; Nixon Peabody LLP

(57) ABSTRACT

The present invention provides methods of generating a mammalian cell that is homozygous at a locus of interest, as well as cells made by the method. The present invention further provides methods of using the cells.

9 Claims, 46 Drawing Sheets

Figure 3A

Class I HLA alleles

| HLA-A | HLA-B | HLA-C | HLA-E | HLA-F | HLA-G |
|---|---|---|---|---|---|
| A*01010101 | B*070201 | Cw*010201 | E*01010101 | F*01010101 | G*01010101 |
| A*01010102N | B*070202 | Cw*010202 | E*01010102 | F*01010102 | G*01010102 |
| A*010102 | B*070203 | Cw*010203 | E*01010103 | F*01010103 | G*01010103 |
| A*01013 | B*070204 | Cw*010204 | E*01030101 | F*01010104 | G*01010104 |
| A*010104 | B*0703 | Cw*0103 | E*01030102 | F*01010105 | G*01010105 |
| A*0102 | B*0704 | Cw*0104 | E*010302 | F*01010106 | G*01010201 |
| A*0103 | B*070501 | Cw*0105 | E*010303 | F*01010107 | G*01010202 |
| A*0104N | B*070502 | Cw*0106 | E*010304 | F*01010108 | G*010103 |
| A*0106 | B*070503 | Cw*0107 | E*0104 | F*01010201 | G*010104 |
| A*0107 | B*0706 | Cw*0108 |  | F*01010202 | G*010105 |
| A*0108 | B*0707 | Cw*0109 |  | F*01010203 | G*010106 |
| A*0109 | B*0708 | Cw*0110 |  | F*01010204 | G*010107 |
| A*0110 | B*0709 | Cw*0111 |  | F*01010205 | G*010108 |
| A*0111N | B*0710 | Cw*0112 |  | F*01010301 | G*010109 |
| A*0112 | B*0711 | Cw*0113 |  | F*01010302 | G*010110 |
| A*0113 | B*0712 | Cw*020201 |  | F*01010303 | G*0102 |
| A*0114 | B*0713 | Cw*020202 |  | F*01010304 | G*0103 |
| A*0115N | B*0714 | Cw*020203 |  | F*0102 | G*010401 |
| A*0116N | B*0715 | Cw*020205 |  | F*01030101 | G*010402 |
| A*0117 | B*0716 | Cw*0203 |  | F*01030102 | G*010403 |
| A*0118N | B*0717 | Cw*0204 |  | F*0104 | G*0105N |
| A*0119 | B*0718 | Cw*0205 |  |  | G*0106 |
| A*0120 | B*0719 | Cw*0206 |  |  | G*0107 |
| A*02010101 | B*0720 | Cw*0207 |  |  |  |
| A*02010102L | B*0721 | Cw*0208 |  |  |  |
| A*020102 | B*0722 | Cw*0209 |  |  |  |
| A*020103 | B*0723 | Cw*0210 |  |  |  |
| A*020104 | B*0724 | Cw*0211 |  |  |  |
| A*020105 | B*0725 | Cw*0212 |  |  |  |
| A*020106 | B*0726 | Cw*0213 |  |  |  |
| A*020107 | B*0727 | Cw*0214 |  |  |  |
| A*020108 | B*0728 | Cw*0215 |  |  |  |

Figure 3B

| HLA-A | HLA-B | HLA-C | HLA-E | HLA-F | HLA-G |
|---|---|---|---|---|---|
| A*020109 | B*0729 | Cw*0216 | | | |
| A*020110 | B*0730 | Cw*0217 | | | |
| A*020111 | B*0731 | Cw*030201 | | | |
| A*020112 | B*0732 | Cw*030202 | | | |
| A*0202 | B*0733 | Cw*030301 | | | |
| A*020301 | B*0734 | Cw*030302 | | | |
| A*020302 | B*0735 | Cw*030303 | | | |
| A*0204 | B*0736 | Cw*030304 | | | |
| A*0205 | B*0737 | Cw*030305 | | | |
| A*020601 | B*0738 | Cw*030401 | | | |
| A*020602 | B*0739 | Cw*030402 | | | |
| A*020603 | B*0740 | Cw*030403 | | | |
| A*0207 | B*0741 | Cw*030404 | | | |
| A*0208 | B*0742 | Cw*030405 | | | |
| A*0209 | B*0743 | Cw*0305 | | | |
| A*0210 | B*0744 | Cw*0306 | | | |
| A*0211 | B*0745 | Cw*0307 | | | |
| A*0212 | B*0746 | Cw*0308 | | | |
| A*0213 | B*0747 | Cw*0309 | | | |
| A*0214 | B*0748 | Cw*0310 | | | |
| A*0215N | B*0749N | Cw*031101 | | | |
| A*0216 | B*0750 | Cw*031102 | | | |
| A*021701 | B*0751 | Cw*0312 | | | |
| A*021702 | B*080101 | Cw*0313 | | | |
| A*0218 | B*080102 | Cw*0314 | | | |
| A*0219 | B*080103 | Cw*0315 | | | |
| A*022001 | B*0802 | Cw*0316 | | | |
| A*022002 | B*0803 | Cw*0317 | | | |
| A*0221 | B*0804 | Cw*0318 | | | |
| A*0222 | B*0805 | Cw*0319 | | | |
| A*0224 | B*0806 | Cw*0320N | | | |
| A*0225 | B*0807 | Cw*0321 | | | |
| A*0226 | B*0808N | Cw*0322Q | | | |

Figure 3C

| HLA-A | HLA-B | HLA-C | HLA-E | HLA-F | HLA-G |
|---|---|---|---|---|---|
| A*0227 | B*0809 | Cw*0323 | | | |
| A*0228 | B*0810 | Cw*0324 | | | |
| A*0229 | B*0811 | Cw*0325 | | | |
| A*0230 | B*0812 | Cw*0326 | | | |
| A*0231 | B*0813 | Cw*0327 | | | |
| A*0232N | B*0814 | Cw*0328 | | | |
| A*0233 | B*0815 | Cw*0329 | | | |
| A*0234 | B*0816 | Cw*0330 | | | |
| A*023501 | B*0817 | Cw*0331 | | | |
| A*023502 | B*0818 | Cw*0332 | | | |
| A*0236 | B*0819N | Cw*0333 | | | |
| A*0237 | B*0820 | Cw*0334 | | | |
| A*0238 | B*0821 | Cw*0335 | | | |
| A*0239 | B*0822 | Cw*04010101 | | | |
| A*0240 | B*0823 | Cw*04010102 | | | |
| A*0241 | B*0824 | Cw*040102 | | | |
| A*0242 | B*0825 | Cw*040103 | | | |
| A*0243N | B*0826 | Cw*040104 | | | |
| A*0244 | B*0827 | Cw*0403 | | | |
| A*0245 | B*0828 | Cw*040401 | | | |
| A*0246 | B*0829 | Cw*040402 | | | |
| A*0247 | B*0830N | Cw*0405 | | | |
| A*0248 | B*0831 | Cw*0406 | | | |
| A*0249 | B*1301 | Cw*0407 | | | |
| A*0250 | B*130201 | Cw*0408 | | | |
| A*0251 | B*130202 | Cw*0409N | | | |
| A*0252 | B*130203 | Cw*0410 | | | |
| A*0253N | B*1303 | Cw*0411 | | | |
| A*0254 | B*1304 | Cw*0412 | | | |
| A*0255 | B*1306 | Cw*0413 | | | |
| A*0256 | B*1307N | Cw*0414 | | | |
| A*0257 | B*1308 | Cw*0415 | | | |
| A*0258 | B*1309 | Cw*0416 | | | |

Figure 3D

| HLA-A | HLA-B | HLA-C | HLA-E | HLA-F | HLA-G |
|---|---|---|---|---|---|
| A*0259 | B*1310 | Cw*0417 | | | |
| A*0260 | B*1311 | Cw*0418 | | | |
| A*0261 | B*1312 | Cw*0419 | | | |
| A*0262 | B*1313 | Cw*0420 | | | |
| A*0263 | B*1314 | Cw*0421 | | | |
| A*0264 | B*1315 | Cw*0423 | | | |
| A*0265 | B*1316 | Cw*0424 | | | |
| A*0266 | B*1317 | Cw*050101 | | | |
| A*0267 | B*1401 | Cw*050102 | | | |
| A*0268 | B*140201 | Cw*050103 | | | |
| A*0269 | B*140202 | Cw*0502 | | | |
| A*0270 | B*1403 | Cw*0503 | | | |
| A*0271 | B*1404 | Cw*0504 | | | |
| A*0272 | B*1405 | Cw*0505 | | | |
| A*0273 | B*140601 | Cw*0506 | | | |
| A*027401 | B*140602 | Cw*0507N | | | |
| A*027402 | B*1407N | Cw*0508 | | | |
| A*0275 | B*15010101 | Cw*0509 | | | |
| A*0276 | B*15010102N | Cw*0510 | | | |
| A*0277 | B*150102 | Cw*0511 | | | |
| A*0278 | B*150103 | Cw*0512 | | | |
| A*0279 | B*150104 | Cw*0513 | | | |
| A*0280 | B*1502 | Cw*0514 | | | |
| A*0281 | B*1503 | Cw*0515 | | | |
| A*0282N | B*1504 | Cw*06020101 | | | |
| A*0283N | B*1505 | Cw*06020102 | | | |
| A*0284 | B*1506 | Cw*060202 | | | |
| A*0285 | B*1507 | Cw*0603 | | | |
| A*0286 | B*1508 | Cw*0604 | | | |
| A*0287 | B*1509 | Cw*0605 | | | |
| A*0288N | B*1510 | Cw*0606 | | | |
| A*0289 | B*151101 | Cw*0607 | | | |
| A*0290 | B*151102 | Cw*0608 | | | |

Figure 3E

| HLA-A | HLA-B | HLA-C | HLA-E | HLA-F | HLA-G |
|---|---|---|---|---|---|
| A*0291 | B*151103 | Cw*0609 | | | |
| A*0292 | B*1512 | Cw*0610 | | | |
| A*0293 | B*1513 | Cw*0611 | | | |
| A*0294N | B*1514 | Cw*0612 | | | |
| A*0295 | B*1515 | Cw*0613 | | | |
| A*0296 | B*1516 | Cw*0614 | | | |
| A*0297 | B*15170101 | Cw*070101 | | | |
| A*0299 | B*15170102 | Cw*070102 | | | |
| A*03010101 | B*151702 | Cw*070103 | | | |
| A*03010102N | B*1518 | Cw*070104 | | | |
| A*03010103 | B*1519 | Cw*070105 | | | |
| A*030102 | B*1520 | Cw*070106 | | | |
| A*030103 | B*1521 | Cw*070107 | | | |
| A*030104 | B*1523 | Cw*07020101 | | | |
| A*030105 | B*1524 | Cw*07020102 | | | |
| A*0302 | B*1525 | Cw*07020103 | | | |
| A*0303N | B*1526N | Cw*0703 | | | |
| A*0304 | B*1527 | Cw*070401 | | | |
| A*0305 | B*1528 | Cw*070402 | | | |
| A*0306 | B*1529 | Cw*0705 | | | |
| A*0307 | B*1530 | Cw*0706 | | | |
| A*0308 | B*1531 | Cw*0707 | | | |
| A*0309 | B*1532 | Cw*0708 | | | |
| A*0310 | B*1533 | Cw*0709 | | | |
| A*0311N | B*1534 | Cw*0710 | | | |
| A*0312 | B*1535 | Cw*0711 | | | |
| A*0313 | B*1536 | Cw*0712 | | | |
| A*0314 | B*1537 | Cw*0713 | | | |
| A*0315 | B*1538 | Cw*0714 | | | |
| A*0316 | B*1539 | Cw*0715 | | | |
| A*0317 | B*1540 | Cw*0716 | | | |
| A*0318 | B*1542 | Cw*0717 | | | |
| A*0319 | B*1543 | Cw*0718 | | | |

Figure 3F

| HLA-A | HLA-B | HLA-C | HLA-E | HLA-F | HLA-G |
|---|---|---|---|---|---|
| A*0320 | B*1544 | Cw*0719 | | | |
| A*0321N | B*1545 | Cw*0720 | | | |
| A*0322 | B*1546 | Cw*0721 | | | |
| A*0323 | B*1547 | Cw*0722 | | | |
| A*0324 | B*1548 | Cw*0723 | | | |
| A*0325 | B*1549 | Cw*0724 | | | |
| A*0326 | B*1550 | Cw*0725 | | | |
| A*110101 | B*1551 | Cw*0726 | | | |
| A*110102 | B*1552 | Cw*0727 | | | |
| A*110103 | B*1553 | Cw*0728 | | | |
| A*110104 | B*1554 | Cw*0729 | | | |
| A*110105 | B*1555 | Cw*0730 | | | |
| A*110106 | B*1556 | Cw*0731 | | | |
| A*110201 | B*1557 | Cw*0732N | | | |
| A*110202 | B*1558 | Cw*0733N | | | |
| A*1103 | B*1560 | Cw*0734 | | | |
| A*1104 | B*1561 | Cw*0735 | | | |
| A*1105 | B*1562 | Cw*0736 | | | |
| A*1106 | B*1563 | Cw*0737 | | | |
| A*1107 | B*1564 | Cw*0738 | | | |
| A*1108 | B*1565 | Cw*0739 | | | |
| A*1109 | B*1566 | Cw*0740 | | | |
| A*1110 | B*1567 | Cw*0741 | | | |
| A*1111 | B*1568 | Cw*0742 | | | |
| A*1112 | B*1569 | Cw*0743 | | | |
| A*1113 | B*1570 | Cw*0744 | | | |
| A*1114 | B*1571 | Cw*0745 | | | |
| A*1115 | B*1572 | Cw*080101 | | | |
| A*1116 | B*1573 | Cw*080102 | | | |
| A*1117 | B*1574 | Cw*0802 | | | |
| A*1118 | B*1575 | Cw*0803 | | | |
| A*1119 | B*1576 | Cw*0804 | | | |
| A*1120 | B*1577 | Cw*0805 | | | |

Figure 3G

| HLA-A | HLA-B | HLA-C | HLA-E | HLA-F | HLA-G |
|---|---|---|---|---|---|
| A*1121N | B*1578 | Cw*0806 | | | |
| A*1122 | B*1579N | Cw*0807 | | | |
| A*1123 | B*1580 | Cw*0808 | | | |
| A*1124 | B*1581 | Cw*0809 | | | |
| A*1125 | B*1582 | Cw*0810 | | | |
| A*1126 | B*1583 | Cw*0811 | | | |
| A*1127 | B*1584 | Cw*0812 | | | |
| A*1128 | B*1585 | Cw*0813 | | | |
| A*1129 | B*1586 | Cw*0814 | | | |
| A*2301 | B*1587 | Cw*120201 | | | |
| A*2302 | B*1588 | Cw*120202 | | | |
| A*2303 | B*1589 | Cw*120203 | | | |
| A*2304 | B*1590 | Cw*12030101 | | | |
| A*2305 | B*1591 | Cw*12030102 | | | |
| A*2306 | B*1592 | Cw*120302 | | | |
| A*2307N | B*1593 | Cw*120303 | | | |
| A*2308N | B*1594N | Cw*120304 | | | |
| A*2309 | B*1595 | Cw*120401 | | | |
| A*2310 | B*1596 | Cw*120402 | | | |
| A*2311N | B*1597 | Cw*1205 | | | |
| A*2312 | B*1598 | Cw*1206 | | | |
| A*2313 | B*1599 | Cw*1207 | | | |
| A*2314 | B*9501 | Cw*1208 | | | |
| A*24020101 | B*9502 | Cw*1209 | | | |
| A*24020102L | B*9503 | Cw*1210 | | | |
| A*240202 | B*9504 | Cw*1211 | | | |
| A*240203 | B*9505 | Cw*1212 | | | |
| A*240204 | B*9506 | Cw*1213 | | | |
| A*240205 | B*9507 | Cw*1214 | | | |
| A*240206 | B*9508 | Cw*1215 | | | |
| A*240207 | B*9509 | Cw*1216 | | | |
| A*240208 | B*9510 | Cw*1217 | | | |
| A*240209 | B*9511N | Cw*1218 | | | |

Figure 3H

| HLA-A | HLA-B | HLA-C | HLA-E | HLA-F | HLA-G |
|---|---|---|---|---|---|
| A*240210 | B*9512 | Cw*1219 | | | |
| A*240211 | B*9513 | Cw*140201 | | | |
| A*240212 | B*9514 | Cw*140202 | | | |
| A*240213 | B*9515 | Cw*140203 | | | |
| A*240301 | B*9516 | Cw*140204 | | | |
| A*240302 | B*9517 | Cw*1403 | | | |
| A*2404 | B*9518 | Cw*1404 | | | |
| A*2405 | B*9519 | Cw*1405 | | | |
| A*2406 | B*9520 | Cw*1406 | | | |
| A*2407 | B*9521 | Cw*1407N | | | |
| A*2408 | B*9522 | Cw*1408 | | | |
| A*2409N | B*180101 | Cw*150201 | | | |
| A*2410 | B*180102 | Cw*150202 | | | |
| A*2411N | B*180103 | Cw*150203 | | | |
| A*2413 | B*1802 | Cw*1503 | | | |
| A*2414 | B*1803 | Cw*1504 | | | |
| A*2415 | B*1804 | Cw*150501 | | | |
| A*2417 | B*1805 | Cw*150502 | | | |
| A*2418 | B*1806 | Cw*150503 | | | |
| A*2419 | B*1807 | Cw*150504 | | | |
| A*2420 | B*1808 | Cw*1506 | | | |
| A*2421 | B*1809 | Cw*1507 | | | |
| A*2422 | B*1810 | Cw*1508 | | | |
| A*2423 | B*1811 | Cw*1509 | | | |
| A*2424 | B*1812 | Cw*1510 | | | |
| A*2425 | B*1813 | Cw*1511 | | | |
| A*2426 | B*1814 | Cw*1512 | | | |
| A*2427 | B*1815 | Cw*1513 | | | |
| A*2428 | B*1817N | Cw*1514 | | | |
| A*2429 | B*1818 | Cw*1515 | | | |
| A*2430 | B*1819 | Cw*1516 | | | |
| A*2431 | B*1820 | Cw*1517 | | | |
| A*2432 | B*1821 | Cw*160101 | | | |

Figure 3I

| HLA-A | HLA-B | HLA-C | HLA-E | HLA-F | HLA-G |
|---|---|---|---|---|---|
| A*2433 | B*1822 | Cw*160102 | | | |
| A*2434 | B*1823N | Cw*1602 | | | |
| A*2435 | B*1824 | Cw*160401 | | | |
| A*2436N | B*2701 | Cw*1606 | | | |
| A*2437 | B*2702 | Cw*1607 | | | |
| A*2438 | B*2703 | Cw*1608 | | | |
| A*2439 | B*270401 | Cw*1609 | | | |
| A*2440N | B*270402 | Cw*1701 | | | |
| A*2441 | B*270502 | Cw*1702 | | | |
| A*2442 | B*270503 | Cw*1703 | | | |
| A*2443 | B*270504 | Cw*1704 | | | |
| A*2444 | B*270505 | Cw*1801 | | | |
| A*2445N | B*270506 | Cw*1802 | | | |
| A*2446 | B*270507 | | | | |
| A*2447 | B*270508 | | | | |
| A*2448N | B*270509 | | | | |
| A*2449 | B*2706 | | | | |
| A*2450 | B*2707 | | | | |
| A*2451 | B*2708 | | | | |
| A*2452 | B*2709 | | | | |
| A*2453 | B*2710 | | | | |
| A*2454 | B*2711 | | | | |
| A*2455 | B*2712 | | | | |
| A*2456 | B*2713 | | | | |
| A*2457 | B*2714 | | | | |
| A*2458 | B*2715 | | | | |
| A*2459 | B*2716 | | | | |
| A*2460N | B*2717 | | | | |
| A*2461 | B*2718 | | | | |
| A*2462 | B*2719 | | | | |
| A*2463 | B*2720 | | | | |
| A*2464 | B*2721 | | | | |
| A*2465 | B*2723 | | | | |

Figure 3J

| HLA-A | HLA-B | HLA-C | HLA-E | HLA-F | HLA-G |
|---|---|---|---|---|---|
| A*2466 | B*2724 | | | | |
| A*2467 | B*2725 | | | | |
| A*2468 | B*2726 | | | | |
| A*250101 | B*2727 | | | | |
| A*250102 | B*2728 | | | | |
| A*2502 | B*2729 | | | | |
| A*2503 | B*2730 | | | | |
| A*2504 | B*2731 | | | | |
| A*2505 | B*2732 | | | | |
| A*2506 | B*2733 | | | | |
| A*260101 | B*2734 | | | | |
| A*260102 | B*2735 | | | | |
| A*260103 | B*2736 | | | | |
| A*260104 | B*350101 | | | | |
| A*2602 | B*350102 | | | | |
| A*2603 | B*350103 | | | | |
| A*2604 | B*350104 | | | | |
| A*2605 | B*350105 | | | | |
| A*2606 | B*350106 | | | | |
| A*260701 | B*350201 | | | | |
| A*260702 | B*350202 | | | | |
| A*2608 | B*3503 | | | | |
| A*2609 | B*350401 | | | | |
| A*2610 | B*350402 | | | | |
| A*2611N | B*3505 | | | | |
| A*2612 | B*3506 | | | | |
| A*2613 | B*3507 | | | | |
| A*2614 | B*350801 | | | | |
| A*2615 | B*350802 | | | | |
| A*2616 | B*350901 | | | | |
| A*2617 | B*350902 | | | | |
| A*2618 | B*3510 | | | | |
| A*2619 | B*3511 | | | | |

Figure 3K

| HLA-A | HLA-B | HLA-C | HLA-E | HLA-F | HLA-G |
|---|---|---|---|---|---|
| A*2620 | B*3512 | | | | |
| A*2621 | B*3513 | | | | |
| A*2622 | B*351401 | | | | |
| A*2623 | B*351402 | | | | |
| A*2624 | B*3515 | | | | |
| A*2625N | B*3516 | | | | |
| A*2626 | B*3517 | | | | |
| A*2627 | B*3518 | | | | |
| A*2628 | B*3519 | | | | |
| A*2629 | B*3520 | | | | |
| A*2630 | B*3521 | | | | |
| A*2631 | B*3522 | | | | |
| A*2632 | B*3523 | | | | |
| A*2633 | B*3524 | | | | |
| A*2634 | B*3525 | | | | |
| A*29010101 | B*3526 | | | | |
| A*29010102N | B*3527 | | | | |
| A*290201 | B*3528 | | | | |
| A*290202 | B*3529 | | | | |
| A*290203 | B*3530 | | | | |
| A*2903 | B*3531 | | | | |
| A*2904 | B*3532 | | | | |
| A*2905 | B*3533 | | | | |
| A*2906 | B*3534 | | | | |
| A*2907 | B*3535 | | | | |
| A*2908N | B*3536 | | | | |
| A*2909 | B*3537 | | | | |
| A*2910 | B*3538 | | | | |
| A*2911 | B*3539 | | | | |
| A*2912 | B*3540N | | | | |
| A*2913 | B*3541 | | | | |
| A*2914 | B*3542 | | | | |
| A*2915 | B*3543 | | | | |

Figure 3L

| HLA-A | HLA-B | HLA-C | HLA-E | HLA-F | HLA-G |
|---|---|---|---|---|---|
| A*2916 | B*3544 | | | | |
| A*300101 | B*3545 | | | | |
| A*300102 | B*3546 | | | | |
| A*300201 | B*3547 | | | | |
| A*300202 | B*3548 | | | | |
| A*300203 | B*3549 | | | | |
| A*3003 | B*3550 | | | | |
| A*3004 | B*3551 | | | | |
| A*3006 | B*3552 | | | | |
| A*3007 | B*3553N | | | | |
| A*3008 | B*3554 | | | | |
| A*3009 | B*3555 | | | | |
| A*3010 | B*3556 | | | | |
| A*3011 | B*3557 | | | | |
| A*3012 | B*3558 | | | | |
| A*3013 | B*3559 | | | | |
| A*3014L | B*3560 | | | | |
| A*3015 | B*3561 | | | | |
| A*3016 | B*3562 | | | | |
| A*3017 | B*3563 | | | | |
| A*3018 | B*3564 | | | | |
| A*3019 | B*3565Q | | | | |
| A*310102 | B*3566 | | | | |
| A*3102 | B*3567 | | | | |
| A*3103 | B*3568 | | | | |
| A*3104 | B*3569 | | | | |
| A*3105 | B*3570 | | | | |
| A*3106 | B*3571 | | | | |
| A*3107 | B*3572 | | | | |
| A*3108 | B*370101 | | | | |
| A*3109 | B*370102 | | | | |
| A*3110 | B*370103 | | | | |
| A*3111 | B*370104 | | | | |

Figure 3M

| HLA-A | HLA-B | HLA-C | HLA-E | HLA-F | HLA-G |
|---|---|---|---|---|---|
| A*3112 | B*3702 | | | | |
| A*3113 | B*3703N | | | | |
| A*3114N | B*3704 | | | | |
| A*3115 | B*3705 | | | | |
| A*3201 | B*3706 | | | | |
| A*3202 | B*3707 | | | | |
| A*3203 | B*3708 | | | | |
| A*3204 | B*3709 | | | | |
| A*3205 | B*3710 | | | | |
| A*3206 | B*3711 | | | | |
| A*3207 | B*3712 | | | | |
| A*3208 | B*380101 | | | | |
| A*3209 | B*380102 | | | | |
| A*3210 | B*380201 | | | | |
| A*3211Q | B*380202 | | | | |
| A*3212 | B*3803 | | | | |
| A*3213 | B*3804 | | | | |
| A*3214 | B*3805 | | | | |
| A*3301 | B*3806 | | | | |
| A*330301 | B*3807 | | | | |
| A*330302 | B*3808 | | | | |
| A*3304 | B*3809 | | | | |
| A*3305 | B*3810 | | | | |
| A*3306 | B*3811 | | | | |
| A*3307 | B*3812 | | | | |
| A*3308 | B*3813 | | | | |
| A*3309 | B*3814 | | | | |
| A*3401 | B*3815 | | | | |
| A*3402 | B*39010101 | | | | |
| A*3403 | B*39010102L | | | | |
| A*3404 | B*390103 | | | | |
| A*3405 | B*390104 | | | | |
| A*3406 | B*390201 | | | | |

Figure 3N

| HLA-A | HLA-B | HLA-C | HLA-E | HLA-F | HLA-G |
|---|---|---|---|---|---|
| A*3407 | B*390202 | | | | |
| A*3408 | B*3903 | | | | |
| A*3601 | B*3904 | | | | |
| A*3602 | B*3905 | | | | |
| A*3603 | B*390601 | | | | |
| A*3604 | B*390602 | | | | |
| A*4301 | B*3907 | | | | |
| A*6601 | B*3908 | | | | |
| A*6602 | B*3909 | | | | |
| A*6603 | B*3910 | | | | |
| A*6604 | B*3911 | | | | |
| A*6605 | B*3912 | | | | |
| A*6606 | B*391301 | | | | |
| A*680101 | B*391302 | | | | |
| A*680102 | B*3914 | | | | |
| A*680103 | B*3915 | | | | |
| A*680104 | B*3916 | | | | |
| A*680105 | B*3917 | | | | |
| A*68020101 | B*3918 | | | | |
| A*68020102 | B*3919 | | | | |
| A*680301 | B*3920 | | | | |
| A*680302 | B*3922 | | | | |
| A*6804 | B*3923 | | | | |
| A*6805 | B*3924 | | | | |
| A*6806 | B*3925N | | | | |
| A*6807 | B*3926 | | | | |
| A*6808 | B*3927 | | | | |
| A*6809 | B*3928 | | | | |
| A*6810 | B*3929 | | | | |
| A*6811N | B*3930 | | | | |
| A*6812 | B*3931 | | | | |
| A*6813 | B*3932 | | | | |
| A*6814 | B*3933 | | | | |

Figure 30

| HLA-A | HLA-B | HLA-C | HLA-E | HLA-F | HLA-G |
|---|---|---|---|---|---|
| A*6815 | B*3934 | | | | |
| A*6816 | B*3935 | | | | |
| A*6817 | B*3936 | | | | |
| A*6818N | B*3937 | | | | |
| A*6819 | B*3938Q | | | | |
| A*6820 | B*3939 | | | | |
| A*6821 | B*3940N | | | | |
| A*6822 | B*3941 | | | | |
| A*6823 | B*400101 | | | | |
| A*6824 | B*400102 | | | | |
| A*6825 | B*400103 | | | | |
| A*6826 | B*400104 | | | | |
| A*6827 | B*400105 | | | | |
| A*6828 | B*400201 | | | | |
| A*6829 | B*400202 | | | | |
| A*6830 | B*400203 | | | | |
| A*6831 | B*4003 | | | | |
| A*6832 | B*4004 | | | | |
| A*6833 | B*4005 | | | | |
| A*6834 | B*40060101 | | | | |
| A*6835 | B*40060102 | | | | |
| A*6836 | B*400602 | | | | |
| A*6901 | B*4007 | | | | |
| A*7401 | B*4008 | | | | |
| A*7402 | B*4009 | | | | |
| A*7403 | B*4010 | | | | |
| A*7404 | B*4011 | | | | |
| A*7405 | B*4012 | | | | |
| A*7406 | B*4013 | | | | |
| A*7407 | B*401401 | | | | |
| A*7408 | B*401402 | | | | |
| A*7409 | B*401403 | | | | |
| A*7410 | B*4015 | | | | |

Figure 3P

| HLA-A | HLA-B | HLA-C | HLA-E | HLA-F | HLA-G |
|---|---|---|---|---|---|
| A*7411 | B*4016 | | | | |
| A*7412N | B*4018 | | | | |
| A*8001 | B*4019 | | | | |
| A*9201 | B*4020 | | | | |
| A*9202 | B*4021 | | | | |
| A*9203 | B*4022N | | | | |
| A*9204 | B*4023 | | | | |
| A*9205 | B*4024 | | | | |
| A*9206 | B*4025 | | | | |
| A*9207 | B*4026 | | | | |
| A*9208 | B*4027 | | | | |
| A*9209 | B*4028 | | | | |
| | B*4029 | | | | |
| | B*4030 | | | | |
| | B*4031 | | | | |
| | B*4032 | | | | |
| | B*4033 | | | | |
| | B*4034 | | | | |
| | B*4035 | | | | |
| | B*4036 | | | | |
| | B*4037 | | | | |
| | B*4038 | | | | |
| | B*4039 | | | | |
| | B*4040 | | | | |
| | B*4042 | | | | |
| | B*4043 | | | | |
| | B*4044 | | | | |
| | B*4045 | | | | |
| | B*4046 | | | | |
| | B*4047 | | | | |
| | B*4048 | | | | |
| | B*4049 | | | | |
| | B*4050 | | | | |

Figure 3Q

| HLA-A | HLA-B | HLA-C | HLA-E | HLA-F | HLA-G |
|---|---|---|---|---|---|
| | B*4051 | | | | |
| | B*4052 | | | | |
| | B*4053 | | | | |
| | B*4054 | | | | |
| | B*4055 | | | | |
| | B*4056 | | | | |
| | B*4057 | | | | |
| | B*4058 | | | | |
| | B*4059 | | | | |
| | B*4060 | | | | |
| | B*4061 | | | | |
| | B*4062 | | | | |
| | B*4063 | | | | |
| | B*4064 | | | | |
| | B*4065 | | | | |
| | B*4066 | | | | |
| | B*4067 | | | | |
| | B*4068 | | | | |
| | B*4069 | | | | |
| | B*4070 | | | | |
| | B*4101 | | | | |
| | B*4102 | | | | |
| | B*4103 | | | | |
| | B*4104 | | | | |
| | B*4105 | | | | |
| | B*4106 | | | | |
| | B*4107 | | | | |
| | B*4108 | | | | |
| | B*4201 | | | | |
| | B*4202 | | | | |
| | B*4204 | | | | |
| | B*420501 | | | | |
| | B*420502 | | | | |

Figure 3R

| HLA-A | HLA-B | HLA-C | HLA-E | HLA-F | HLA-G |
|---|---|---|---|---|---|
| | B*4206 | | | | |
| | B*4207 | | | | |
| | B*4208 | | | | |
| | B*4209 | | | | |
| | B*440201O1 | | | | |
| | B*440201O2S | | | | |
| | B*440202 | | | | |
| | B*440203 | | | | |
| | B*440204 | | | | |
| | B*440301 | | | | |
| | B*440302 | | | | |
| | B*4404 | | | | |
| | B*4405 | | | | |
| | B*4406 | | | | |
| | B*4407 | | | | |
| | B*4408 | | | | |
| | B*4409 | | | | |
| | B*4410 | | | | |
| | B*4411 | | | | |
| | B*4412 | | | | |
| | B*4413 | | | | |
| | B*4414 | | | | |
| | B*4415 | | | | |
| | B*4416 | | | | |
| | B*4417 | | | | |
| | B*4418 | | | | |
| | B*4419N | | | | |
| | B*4420 | | | | |
| | B*4421 | | | | |
| | B*4422 | | | | |
| | B*4423N | | | | |
| | B*4424 | | | | |
| | B*4425 | | | | |

Figure 3S

| HLA-A | HLA-B | HLA-C | HLA-E | HLA-F | HLA-G |
|---|---|---|---|---|---|
| | B*4426 | | | | |
| | B*4427 | | | | |
| | B*4428 | | | | |
| | B*4429 | | | | |
| | B*4430 | | | | |
| | B*4431 | | | | |
| | B*4432 | | | | |
| | B*4433 | | | | |
| | B*4434 | | | | |
| | B*4435 | | | | |
| | B*4436 | | | | |
| | B*4437 | | | | |
| | B*4438 | | | | |
| | B*4439 | | | | |
| | B*4440 | | | | |
| | B*4441 | | | | |
| | B*4442 | | | | |
| | B*4443 | | | | |
| | B*4444 | | | | |
| | B*4445 | | | | |
| | B*4446 | | | | |
| | B*4447 | | | | |
| | B*4448 | | | | |
| | B*4449 | | | | |
| | B*4450 | | | | |
| | B*4451 | | | | |
| | B*4501 | | | | |
| | B*4502 | | | | |
| | B*4503 | | | | |
| | B*4504 | | | | |
| | B*4505 | | | | |
| | B*4506 | | | | |
| | B*4507 | | | | |

Figure 3T

| HLA-A | HLA-B | HLA-C | HLA-E | HLA-F | HLA-G |
|---|---|---|---|---|---|
| | B*460101 | | | | |
| | B*460102 | | | | |
| | B*4602 | | | | |
| | B*4603 | | | | |
| | B*4604 | | | | |
| | B*4605 | | | | |
| | B*4606 | | | | |
| | B*4607N | | | | |
| | B*4608 | | | | |
| | B*4609 | | | | |
| | B*47010101 | | | | |
| | B*47010102 | | | | |
| | B*4702 | | | | |
| | B*4703 | | | | |
| | B*4704 | | | | |
| | B*4705 | | | | |
| | B*4801 | | | | |
| | B*4802 | | | | |
| | B*480301 | | | | |
| | B*480302 | | | | |
| | B*4804 | | | | |
| | B*4805 | | | | |
| | B*4806 | | | | |
| | B*4807 | | | | |
| | B*4808 | | | | |
| | B*4809 | | | | |
| | B*4810 | | | | |
| | B*4811 | | | | |
| | B*4812 | | | | |
| | B*4813 | | | | |
| | B*4814 | | | | |
| | B*4815 | | | | |
| | B*4816 | | | | |

Figure 3U

| HLA-A | HLA-B | HLA-C | HLA-E | HLA-F | HLA-G |
|---|---|---|---|---|---|
| | B*4901 | | | | |
| | B*4902 | | | | |
| | B*4903 | | | | |
| | B*4904 | | | | |
| | B*4905 | | | | |
| | B*5001 | | | | |
| | B*5002 | | | | |
| | B*5004 | | | | |
| | B*510101 | | | | |
| | B*510102 | | | | |
| | B*510103 | | | | |
| | B*510104 | | | | |
| | B*510105 | | | | |
| | B*510106 | | | | |
| | B*510107 | | | | |
| | B*510201 | | | | |
| | B*510202 | | | | |
| | B*5103 | | | | |
| | B*5104 | | | | |
| | B*5105 | | | | |
| | B*5106 | | | | |
| | B*5107 | | | | |
| | B*5108 | | | | |
| | B*5109 | | | | |
| | B*5110 | | | | |
| | B*5111N | | | | |
| | B*5112 | | | | |
| | B*511301 | | | | |
| | B*511302 | | | | |
| | B*5114 | | | | |
| | B*5115 | | | | |
| | B*5116 | | | | |
| | B*5117 | | | | |

Figure 3V

| HLA-A | HLA-B | HLA-C | HLA-E | HLA-F | HLA-G |
|---|---|---|---|---|---|
| | B*5118 | | | | |
| | B*5119 | | | | |
| | B*5120 | | | | |
| | B*5121 | | | | |
| | B*5122 | | | | |
| | B*5123 | | | | |
| | B*5124 | | | | |
| | B*5126 | | | | |
| | B*5127N | | | | |
| | B*5128 | | | | |
| | B*5129 | | | | |
| | B*5130 | | | | |
| | B*5131 | | | | |
| | B*5132 | | | | |
| | B*5133 | | | | |
| | B*5134 | | | | |
| | B*5135 | | | | |
| | B*5136 | | | | |
| | B*5137 | | | | |
| | B*5138 | | | | |
| | B*5139 | | | | |
| | B*5140 | | | | |
| | B*5141N | | | | |
| | B*5142 | | | | |
| | B*5143 | | | | |
| | B*5144N | | | | |
| | B*5145 | | | | |
| | B*5146 | | | | |
| | B*520101 | | | | |
| | B*520102 | | | | |
| | B*520103 | | | | |
| | B*520104 | | | | |
| | B*5202 | | | | |

Figure 3W

| HLA-A | HLA-B | HLA-C | HLA-E | HLA-F | HLA-G |
|---|---|---|---|---|---|
| | B*5203 | | | | |
| | B*5204 | | | | |
| | B*5205 | | | | |
| | B*5206 | | | | |
| | B*5207 | | | | |
| | B*5208 | | | | |
| | B*5209 | | | | |
| | B*5210 | | | | |
| | B*530101 | | | | |
| | B*530102 | | | | |
| | B*530103 | | | | |
| | B*530104 | | | | |
| | B*5302 | | | | |
| | B*5303 | | | | |
| | B*5304 | | | | |
| | B*5305 | | | | |
| | B*5306 | | | | |
| | B*5307 | | | | |
| | B*5308 | | | | |
| | B*5309 | | | | |
| | B*5310 | | | | |
| | B*5311 | | | | |
| | B*5312 | | | | |
| | B*5401 | | | | |
| | B*5402 | | | | |
| | B*5403 | | | | |
| | B*5404 | | | | |
| | B*5405N | | | | |
| | B*5406 | | | | |
| | B*5407 | | | | |
| | B*5408N | | | | |
| | B*5409 | | | | |
| | B*5410 | | | | |

Figure 3X

| HLA-A | HLA-B | HLA-C | HLA-E | HLA-F | HLA-G |
|---|---|---|---|---|---|
| | B*5411 | | | | |
| | B*5412 | | | | |
| | B*550101 | | | | |
| | B*550102 | | | | |
| | B*550103 | | | | |
| | B*550104 | | | | |
| | B*550201 | | | | |
| | B*550202 | | | | |
| | B*5503 | | | | |
| | B*5504 | | | | |
| | B*5505 | | | | |
| | B*5507 | | | | |
| | B*5508 | | | | |
| | B*5509 | | | | |
| | B*5510 | | | | |
| | B*5511 | | | | |
| | B*5512 | | | | |
| | B*5513 | | | | |
| | B*5514 | | | | |
| | B*5515 | | | | |
| | B*5516 | | | | |
| | B*5517 | | | | |
| | B*5518 | | | | |
| | B*5519 | | | | |
| | B*5520 | | | | |
| | B*5521 | | | | |
| | B*5522 | | | | |
| | B*5523 | | | | |
| | B*5524 | | | | |
| | B*5601 | | | | |
| | B*5602 | | | | |
| | B*5603 | | | | |
| | B*5604 | | | | |

Figure 3Y

| HLA-A | HLA-B | HLA-C | HLA-E | HLA-F | HLA-G |
|---|---|---|---|---|---|
| | B*560501 | | | | |
| | B*560502 | | | | |
| | B*5606 | | | | |
| | B*5607 | | | | |
| | B*5608 | | | | |
| | B*5609 | | | | |
| | B*5610 | | | | |
| | B*5611 | | | | |
| | B*5612 | | | | |
| | B*5613 | | | | |
| | B*5614 | | | | |
| | B*5615 | | | | |
| | B*5616 | | | | |
| | B*5617 | | | | |
| | B*5618 | | | | |
| | B*5619N | | | | |
| | B*570101 | | | | |
| | B*570102 | | | | |
| | B*570103 | | | | |
| | B*5702 | | | | |
| | B*570301 | | | | |
| | B*570302 | | | | |
| | B*5704 | | | | |
| | B*5705 | | | | |
| | B*5706 | | | | |
| | B*5707 | | | | |
| | B*5708 | | | | |
| | B*5709 | | | | |
| | B*5710 | | | | |
| | B*5711 | | | | |
| | B*5801 | | | | |
| | B*5802 | | | | |
| | B*5804 | | | | |

Figure 3Z

| HLA-A | HLA-B | HLA-C | HLA-E | HLA-F | HLA-G |
|---|---|---|---|---|---|
| | B*5805 | | | | |
| | B*5806 | | | | |
| | B*5807 | | | | |
| | B*5808 | | | | |
| | B*5809 | | | | |
| | B*5810N | | | | |
| | B*5811 | | | | |
| | B*5812 | | | | |
| | B*5813 | | | | |
| | B*5814 | | | | |
| | B*5901 | | | | |
| | B*5902 | | | | |
| | B*670101 | | | | |
| | B*670102 | | | | |
| | B*6702 | | | | |
| | B*7301 | | | | |
| | B*7801 | | | | |
| | B*780201 | | | | |
| | B*780202 | | | | |
| | B*7803 | | | | |
| | B*7804 | | | | |
| | B*7805 | | | | |
| | B*8101 | | | | |
| | B*8102 | | | | |
| | B*8201 | | | | |
| | B*8202 | | | | |
| | B*8301 | | | | |

| HLA-H | HLA-J | HLA-K | HLA-L | HLA-P |
|---|---|---|---|---|
| H*01010101 | J*01010101 | K*01010101 | L*01010101 | P*01010101 |
| H*01010102 | J*01010102 | K*01010102 | L*01010102 | P*01010102 |
| H*01010103 | J*01010103 | K*01010103 | L*01010103 | P*02010101 |
| H*0102 | J*01010104 | K*01010104 | L*010102 | P*02010102 |
| H*02010101 | J*01010105 | K*0102 | L*0102 | |

Figure 3AA

| HLA-H | HLA-J | HLA-K | HLA-L | HLA-P |
|---|---|---|---|---|
| H*02010102 | J*01010106 | K*0103 | | |
| H*0202 | J*01010107 | | | |
| H*0203 | J*01010108 | | | |
| H*0204 | J*0201 | | | |
| H*0205 | | | | |
| H*0206 | | | | |
| H*0301 | | | | |

Figure 4A

Class II HLA alleles

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| DRA*0101 | DRB1*010101 | DRB2*0101 | DQA1*010101 | DQB1*050101 | DPA1*010301 | DPB1*010101 |
| DRA*010201 | DRB1*010102 | DRB3*01010201 | DQA1*010102 | DQB1*050102 | DPA1*010302 | DPB1*010102 |
| DRA*010202 | DRB1*010103 | DRB3*01010202 | DQA1*010201 | DQB1*050201 | DPA1*010303 | DPB1*010103 |
|  | DRB1*010201 | DRB3*010103 | DQA1*010202 | DQB1*050202 | DPA1*0104 | DPB1*0102 |
|  | DRB1*010202 | DRB3*010104 | DQA1*010203 | DQB1*050301 | DPA1*0105 | DPB1*020102 |
|  | DRB1*010203 | DRB3*0102 | DQA1*010204 | DQB1*050302 | DPA1*0106 | DPB1*020103 |
|  | DRB1*010204 | DRB3*0103 | DQA1*0103 | DQB1*0504 | DPA1*0107 | DPB1*020104 |
|  | DRB1*0103 | DRB3*0104 | DQA1*010401 | DQB1*0505 | DPA1*0108 | DPB1*020105 |
|  | DRB1*0104 | DRB3*0105 | DQA1*010402 | DQB1*020101 | DPA1*0109 | DPB1*020106 |
|  | DRB1*0105 | DRB3*0106 | DQA1*0105 | DQB1*020102 | DPA1*020101 | DPB1*0202 |
|  | DRB1*0106 | DRB3*0107 | DQA1*0106 | DQB1*0202 | DPA1*020102 | DPB1*0203 |
|  | DRB1*0107 | DRB3*0108 | DQA1*0107 | DQB1*0203 | DPA1*020103 | DPB1*030101 |
|  | DRB1*0108 | DRB3*0109 | DQA1*0201 | DQB1*0204 | DPA1*020104 | DPB1*030102 |
|  | DRB1*0109 | DRB3*0110 | DQA1*030101 | DQB1*030101 | DPA1*020105 | DPB1*0302 |
|  | DRB1*0110 | DRB3*0111 | DQA1*0302 | DQB1*030102 | DPA1*020106 | DPB1*040101 |
|  | DRB1*0111 | DRB3*0201 | DQA1*0303 | DQB1*030103 | DPA1*020201 | DPB1*040102 |
|  | DRB1*0112 | DRB3*020201 | DQA1*040101 | DQB1*030201 | DPA1*020202 | DPB1*0402 |
|  | DRB1*0113 | DRB3*020202 | DQA1*040102 | DQB1*030202 | DPA1*020203 | DPB1*0403 |
|  | DRB1*0114 | DRB3*020203 | DQA1*0402 | DQB1*030203 | DPA1*0203 | DPB1*0501 |
|  | DRB1*0115 | DRB3*020204 | DQA1*0403N | DQB1*030204 | DPA1*0301 | DPB1*0502 |
|  | DRB1*0116 | DRB3*020205 | DQA1*0404 | DQB1*030302 | DPA1*0302 | DPB1*0601 |
|  | DRB1*030101 | DRB3*0203 | DQA1*050101 | DQB1*030303 | DPA1*0303 | DPB1*0602 |
|  | DRB1*030102 | DRB3*0204 | DQA1*050102 | DQB1*0304 | DPA1*0401 | DPB1*0801 |
|  | DRB1*030201 | DRB3*0205 | DQA1*0502 | DQB1*030501 |  | DPB1*0802 |
|  | DRB1*030202 | DRB3*0206 | DQA1*0503 | DQB1*030502 |  | DPB1*0901 |
|  | DRB1*0303 | DRB3*0207 | DQA1*0504 | DQB1*030503 |  | DPB1*0902 |
|  | DRB1*0304 | DRB3*0208 | DQA1*0505 | DQB1*030504 |  | DPB1*1001 |
|  | DRB1*030501 | DRB3*0209 | DQA1*0506 | DQB1*0306 |  | DPB1*1002 |
|  | DRB1*030502 | DRB3*0210 | DQA1*0507 | DQB1*0307 |  | DPB1*110101 |
|  | DRB1*0306 | DRB3*0211 | DQA1*0508 | DQB1*0308 |  | DPB1*110102 |
|  | DRB1*0307 | DRB3*0212 | DQA1*0509 | DQB1*0309 |  | DPB1*1102 |
|  | DRB1*0308 | DRB3*0213 | DQA1*060101 | DQB1*0310 |  | DPB1*1301 |
|  | DRB1*0309 | DRB3*0214 | DQA1*060102 | DQB1*0311 |  | DPB1*1302 |
|  | DRB1*0310 | DRB3*0215 | DQA1*0602 | DQB1*0312 |  | DPB1*1401 |

Figure 4B

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*0311 | DRB3*0216 | | DQB1*0313 | | DPB1*1402 |
| | DRB1*0312 | DRB3*0217 | | DQB1*0314 | | DPB1*1501 |
| | DRB1*0313 | DRB3*0218 | | DQB1*0315 | | DPB1*1502 |
| | DRB1*0314 | DRB3*0219 | | DQB1*0316 | | DPB1*1601 |
| | DRB1*0315 | DRB3*0220 | | DQB1*0317 | | DPB1*1602 |
| | DRB1*0316 | DRB3*0221 | | DQB1*0318 | | DPB1*1701 |
| | DRB1*0317 | DRB3*0222 | | DQB1*0319 | | DPB1*1702 |
| | DRB1*0318 | DRB3*030101 | | DQB1*0401 | | DPB1*1801 |
| | DRB1*0319 | DRB3*030102 | | DQB1*0402 | | DPB1*1802 |
| | DRB1*0320 | DRB3*0302 | | DQB1*060101 | | DPB1*1901 |
| | DRB1*0321 | DRB3*0303 | | DQB1*060102 | | DPB1*1902 |
| | DRB1*0322 | DRB4*01010101 | | DQB1*060103 | | DPB1*200101 |
| | DRB1*0323 | DRB4*0102 | | DQB1*0602 | | DPB1*200102 |
| | DRB1*0324 | DRB4*01030101 | | DQB1*060301 | | DPB1*2002 |
| | DRB1*0325 | DRB4*01030102N | | DQB1*060302 | | DPB1*2101 |
| | DRB1*0326 | DRB4*010302 | | DQB1*060401 | | DPB1*2201 |
| | DRB1*0327 | DRB4*010303 | | DQB1*060402 | | DPB1*2301 |
| | DRB1*0328 | DRB4*010304 | | DQB1*060403 | | DPB1*2401 |
| | DRB1*0329 | DRB4*0104 | | DQB1*060501 | | DPB1*2501 |
| | DRB1*0330 | DRB4*0105 | | DQB1*060502 | | DPB1*260101 |
| | DRB1*0331 | DRB4*0106 | | DQB1*0606 | | DPB1*260102 |
| | DRB1*040101 | DRB4*0107 | | DQB1*0607 | | DPB1*2701 |
| | DRB1*040102 | DRB4*0201N | | DQB1*060801 | | DPB1*2801 |
| | DRB1*0402 | DRB4*0301N | | DQB1*060802 | | DPB1*2901 |
| | DRB1*040301 | DRB5*010101 | | DQB1*0609 | | DPB1*3001 |
| | DRB1*040302 | DRB5*010102 | | DQB1*0610 | | DPB1*3101 |
| | DRB1*040303 | DRB5*0102 | | DQB1*061101 | | DPB1*3201 |
| | DRB1*0404 | DRB5*0103 | | DQB1*061102 | | DPB1*3301 |
| | DRB1*040501 | DRB5*0104 | | DQB1*0612 | | DPB1*3401 |
| | DRB1*040502 | DRB5*0105 | | DQB1*0613 | | DPB1*3501 |
| | DRB1*040503 | DRB5*0106 | | DQB1*0614 | | DPB1*3601 |
| | DRB1*040504 | DRB5*0107 | | DQB1*0615 | | DPB1*3701 |
| | DRB1*040601 | DRB5*0108N | | DQB1*0616 | | DPB1*3801 |
| | DRB1*040602 | DRB5*0109 | | DQB1*0617 | | DPB1*3901 |
| | DRB1*040701 | DRB5*0110N | | DQB1*0618 | | DPB1*4001 |
| | DRB1*040702 | DRB5*0111 | | DQB1*0619 | | DPB1*4101 |
| | DRB1*040703 | DRB5*0112 | | DQB1*0620 | | DPB1*4401 |

Figure 4C

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*0408 | DRB5*0113 | | DQB1*0621 | | DPB1*4501 |
| | DRB1*0409 | DRB5*0202 | | DQB1*0622 | | DPB1*4601 |
| | DRB1*0410 | DRB5*0203 | | DQB1*0623 | | DPB1*4701 |
| | DRB1*0411 | DRB5*0204 | | DQB1*0624 | | DPB1*4801 |
| | DRB1*0412 | DRB5*0205 | | DQB1*0625 | | DPB1*4901 |
| | DRB1*0413 | DRB6*0101 | | DQB1*0626N | | DPB1*5001 |
| | DRB1*0414 | DRB6*0201 | | DQB1*0627 | | DPB1*5101 |
| | DRB1*0415 | DRB6*0202 | | DQB1*0628 | | DPB1*5201 |
| | DRB1*0416 | DRB7*010101 | | DQB1*0629 | | DPB1*5301 |
| | DRB1*0417 | DRB7*010102 | | DQB1*0630 | | DPB1*5401 |
| | DRB1*0418 | DRB8*0101 | | | | DPB1*5501 |
| | DRB1*0419 | DRB9*0101 | | | | DPB1*5601 |
| | DRB1*0420 | | | | | DPB1*5701 |
| | DRB1*0421 | | | | | DPB1*5801 |
| | DRB1*0422 | | | | | DPB1*5901 |
| | DRB1*0423 | | | | | DPB1*6001 |
| | DRB1*0424 | | | | | DPB1*6101N |
| | DRB1*0425 | | | | | DPB1*6201 |
| | DRB1*0426 | | | | | DPB1*6301 |
| | DRB1*0427 | | | | | DPB1*6401N |
| | DRB1*0428 | | | | | DPB1*6501 |
| | DRB1*0429 | | | | | DPB1*6601 |
| | DRB1*0430 | | | | | DPB1*6701 |
| | DRB1*0431 | | | | | DPB1*6801 |
| | DRB1*0432 | | | | | DPB1*6901 |
| | DRB1*0433 | | | | | DPB1*7001 |
| | DRB1*0434 | | | | | DPB1*7101 |
| | DRB1*0435 | | | | | DPB1*7201 |
| | DRB1*0436 | | | | | DPB1*7301 |
| | DRB1*0437 | | | | | DPB1*7401 |
| | DRB1*0438 | | | | | DPB1*7501 |
| | DRB1*0439 | | | | | DPB1*7601 |
| | DRB1*0440 | | | | | DPB1*7701 |
| | DRB1*0441 | | | | | DPB1*7801 |
| | DRB1*0442 | | | | | DPB1*7901 |
| | DRB1*0443 | | | | | DPB1*8001 |
| | DRB1*0444 | | | | | DPB1*8101 |

Figure 4D

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*0445 | | | | | |
| | DRB1*0446 | | | | | DPB1*8201 |
| | DRB1*0447 | | | | | DPB1*8301 |
| | DRB1*0448 | | | | | DPB1*8401 |
| | DRB1*0449 | | | | | DPB1*8501 |
| | DRB1*0450 | | | | | DPB1*8601 |
| | DRB1*0451 | | | | | DPB1*8701 |
| | DRB1*0452 | | | | | DPB1*8801 |
| | DRB1*0453 | | | | | DPB1*8901 |
| | DRB1*0454 | | | | | DPB1*9001 |
| | DRB1*0455 | | | | | DPB1*9101 |
| | DRB1*0456 | | | | | DPB1*9201 |
| | DRB1*0457 | | | | | DPB1*9301 |
| | DRB1*0458 | | | | | DPB1*9401 |
| | DRB1*0459 | | | | | DPB1*9501 |
| | DRB1*0460 | | | | | DPB1*9601 |
| | DRB1*0461 | | | | | DPB1*9701 |
| | DRB1*0462 | | | | | DPB1*9801 |
| | DRB1*0463 | | | | | DPB1*9901 |
| | DRB1*070101 | | | | | |
| | DRB1*070102 | | | | | |
| | DRB1*0703 | | | | | |
| | DRB1*0704 | | | | | |
| | DRB1*0705 | | | | | |
| | DRB1*0706 | | | | | |
| | DRB1*0707 | | | | | |
| | DRB1*0708 | | | | | |
| | DRB1*0709 | | | | | |
| | DRB1*0710N | | | | | |
| | DRB1*0711 | | | | | |
| | DRB1*0712 | | | | | |
| | DRB1*080101 | | | | | |
| | DRB1*080102 | | | | | |
| | DRB1*080103 | | | | | |
| | DRB1*080201 | | | | | |
| | DRB1*080202 | | | | | |
| | DRB1*080203 | | | | | |

Figure 4E

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*080302 | | | | | |
| | DRB1*080401 | | | | | |
| | DRB1*080402 | | | | | |
| | DRB1*080403 | | | | | |
| | DRB1*080404 | | | | | |
| | DRB1*0805 | | | | | |
| | DRB1*0806 | | | | | |
| | DRB1*0807 | | | | | |
| | DRB1*0808 | | | | | |
| | DRB1*0809 | | | | | |
| | DRB1*0810 | | | | | |
| | DRB1*0811 | | | | | |
| | DRB1*0812 | | | | | |
| | DRB1*0813 | | | | | |
| | DRB1*0814 | | | | | |
| | DRB1*0815 | | | | | |
| | DRB1*0816 | | | | | |
| | DRB1*0817 | | | | | |
| | DRB1*0818 | | | | | |
| | DRB1*0819 | | | | | |
| | DRB1*0820 | | | | | |
| | DRB1*0821 | | | | | |
| | DRB1*0822 | | | | | |
| | DRB1*0823 | | | | | |
| | DRB1*0824 | | | | | |
| | DRB1*0825 | | | | | |
| | DRB1*0826 | | | | | |
| | DRB1*0827 | | | | | |
| | DRB1*0828 | | | | | |
| | DRB1*0829 | | | | | |
| | DRB1*0830 | | | | | |
| | DRB1*0831 | | | | | |
| | DRB1*0832 | | | | | |
| | DRB1*090102 | | | | | |
| | DRB1*090103 | | | | | |
| | DRB1*0902 | | | | | |
| | DRB1*0903 | | | | | |

Figure 4F

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*0904 | | | | | |
| | DRB1*0905 | | | | | |
| | DRB1*0906 | | | | | |
| | DRB1*100101 | | | | | |
| | DRB1*100102 | | | | | |
| | DRB1*110101 | | | | | |
| | DRB1*110102 | | | | | |
| | DRB1*110103 | | | | | |
| | DRB1*110104 | | | | | |
| | DRB1*110105 | | | | | |
| | DRB1*110106 | | | | | |
| | DRB1*110201 | | | | | |
| | DRB1*110202 | | | | | |
| | DRB1*1103 | | | | | |
| | DRB1*110401 | | | | | |
| | DRB1*110402 | | | | | |
| | DRB1*110403 | | | | | |
| | DRB1*1105 | | | | | |
| | DRB1*110601 | | | | | |
| | DRB1*110602 | | | | | |
| | DRB1*1107 | | | | | |
| | DRB1*110801 | | | | | |
| | DRB1*110802 | | | | | |
| | DRB1*1109 | | | | | |
| | DRB1*1110 | | | | | |
| | DRB1*111101 | | | | | |
| | DRB1*111102 | | | | | |
| | DRB1*111201 | | | | | |
| | DRB1*111202 | | | | | |
| | DRB1*1113 | | | | | |
| | DRB1*111401 | | | | | |
| | DRB1*111402 | | | | | |
| | DRB1*1115 | | | | | |
| | DRB1*1116 | | | | | |
| | DRB1*1117 | | | | | |
| | DRB1*1118 | | | | | |
| | DRB1*111901 | | | | | |

Figure 4G

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*111902 | | | | | |
| | DRB1*1120 | | | | | |
| | DRB1*1121 | | | | | |
| | DRB1*1122 | | | | | |
| | DRB1*1123 | | | | | |
| | DRB1*1124 | | | | | |
| | DRB1*1125 | | | | | |
| | DRB1*1126 | | | | | |
| | DRB1*112701 | | | | | |
| | DRB1*112702 | | | | | |
| | DRB1*1128 | | | | | |
| | DRB1*1129 | | | | | |
| | DRB1*1130 | | | | | |
| | DRB1*1131 | | | | | |
| | DRB1*1132 | | | | | |
| | DRB1*1133 | | | | | |
| | DRB1*1134 | | | | | |
| | DRB1*1135 | | | | | |
| | DRB1*1136 | | | | | |
| | DRB1*1137 | | | | | |
| | DRB1*1138 | | | | | |
| | DRB1*1139 | | | | | |
| | DRB1*1140 | | | | | |
| | DRB1*1141 | | | | | |
| | DRB1*1142 | | | | | |
| | DRB1*1143 | | | | | |
| | DRB1*1144 | | | | | |
| | DRB1*1145 | | | | | |
| | DRB1*1146 | | | | | |
| | DRB1*1147 | | | | | |
| | DRB1*1148 | | | | | |
| | DRB1*1149 | | | | | |
| | DRB1*1150 | | | | | |
| | DRB1*1151 | | | | | |
| | DRB1*1152 | | | | | |
| | DRB1*1153 | | | | | |
| | DRB1*115401 | | | | | |

Figure 4H

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*115402 | | | | | |
| | DRB1*1155 | | | | | |
| | DRB1*1156 | | | | | |
| | DRB1*1157 | | | | | |
| | DRB1*1158 | | | | | |
| | DRB1*1159 | | | | | |
| | DRB1*1160 | | | | | |
| | DRB1*120101 | | | | | |
| | DRB1*120102 | | | | | |
| | DRB1*120201 | | | | | |
| | DRB1*120202 | | | | | |
| | DRB1*120302 | | | | | |
| | DRB1*1204 | | | | | |
| | DRB1*1205 | | | | | |
| | DRB1*1206 | | | | | |
| | DRB1*1207 | | | | | |
| | DRB1*1208 | | | | | |
| | DRB1*1209 | | | | | |
| | DRB1*1210 | | | | | |
| | DRB1*1211 | | | | | |
| | DRB1*1212 | | | | | |
| | DRB1*1213 | | | | | |
| | DRB1*1214 | | | | | |
| | DRB1*1215 | | | | | |
| | DRB1*130101 | | | | | |
| | DRB1*130102 | | | | | |
| | DRB1*130103 | | | | | |
| | DRB1*130201 | | | | | |
| | DRB1*130202 | | | | | |
| | DRB1*130301 | | | | | |
| | DRB1*130302 | | | | | |
| | DRB1*1304 | | | | | |
| | DRB1*130501 | | | | | |
| | DRB1*130502 | | | | | |
| | DRB1*1306 | | | | | |
| | DRB1*130701 | | | | | |
| | DRB1*130702 | | | | | |

Figure 4I

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*1308 | | | | | |
| | DRB1*1309 | | | | | |
| | DRB1*1310 | | | | | |
| | DRB1*1311 | | | | | |
| | DRB1*1312 | | | | | |
| | DRB1*1313 | | | | | |
| | DRB1*131401 | | | | | |
| | DRB1*131402 | | | | | |
| | DRB1*1315 | | | | | |
| | DRB1*1316 | | | | | |
| | DRB1*1317 | | | | | |
| | DRB1*1318 | | | | | |
| | DRB1*1319 | | | | | |
| | DRB1*1320 | | | | | |
| | DRB1*1321 | | | | | |
| | DRB1*1322 | | | | | |
| | DRB1*1323 | | | | | |
| | DRB1*1324 | | | | | |
| | DRB1*1325 | | | | | |
| | DRB1*1326 | | | | | |
| | DRB1*1327 | | | | | |
| | DRB1*1328 | | | | | |
| | DRB1*1329 | | | | | |
| | DRB1*1330 | | | | | |
| | DRB1*1331 | | | | | |
| | DRB1*1332 | | | | | |
| | DRB1*1333 | | | | | |
| | DRB1*1334 | | | | | |
| | DRB1*1335 | | | | | |
| | DRB1*1336 | | | | | |
| | DRB1*1337 | | | | | |
| | DRB1*1338 | | | | | |
| | DRB1*1339 | | | | | |
| | DRB1*1340 | | | | | |
| | DRB1*1341 | | | | | |
| | DRB1*1342 | | | | | |
| | DRB1*1343 | | | | | |

Figure 4J

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*1344 | | | | | |
| | DRB1*1345 | | | | | |
| | DRB1*1346 | | | | | |
| | DRB1*1347 | | | | | |
| | DRB1*1348 | | | | | |
| | DRB1*1349 | | | | | |
| | DRB1*1350 | | | | | |
| | DRB1*1351 | | | | | |
| | DRB1*1352 | | | | | |
| | DRB1*1353 | | | | | |
| | DRB1*1354 | | | | | |
| | DRB1*1355 | | | | | |
| | DRB1*1356 | | | | | |
| | DRB1*1357 | | | | | |
| | DRB1*1358 | | | | | |
| | DRB1*1359 | | | | | |
| | DRB1*1360 | | | | | |
| | DRB1*1361 | | | | | |
| | DRB1*1362 | | | | | |
| | DRB1*1363 | | | | | |
| | DRB1*1364 | | | | | |
| | DRB1*1365 | | | | | |
| | DRB1*1366 | | | | | |
| | DRB1*1367 | | | | | |
| | DRB1*1368 | | | | | |
| | DRB1*1369 | | | | | |
| | DRB1*1370 | | | | | |
| | DRB1*1371 | | | | | |
| | DRB1*1372 | | | | | |
| | DRB1*1373 | | | | | |
| | DRB1*1374 | | | | | |
| | DRB1*1375 | | | | | |
| | DRB1*140101 | | | | | |
| | DRB1*140102 | | | | | |
| | DRB1*140103 | | | | | |
| | DRB1*1402 | | | | | |
| | DRB1*140301 | | | | | |

Figure 4K

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*140302 | | | | | |
| | DRB1*1404 | | | | | |
| | DRB1*140501 | | | | | |
| | DRB1*140502 | | | | | |
| | DRB1*140503 | | | | | |
| | DRB1*1406 | | | | | |
| | DRB1*140701 | | | | | |
| | DRB1*140702 | | | | | |
| | DRB1*1408 | | | | | |
| | DRB1*1409 | | | | | |
| | DRB1*1410 | | | | | |
| | DRB1*1411 | | | | | |
| | DRB1*1412 | | | | | |
| | DRB1*1413 | | | | | |
| | DRB1*1414 | | | | | |
| | DRB1*1415 | | | | | |
| | DRB1*1416 | | | | | |
| | DRB1*1417 | | | | | |
| | DRB1*1418 | | | | | |
| | DRB1*1419 | | | | | |
| | DRB1*1420 | | | | | |
| | DRB1*1421 | | | | | |
| | DRB1*1422 | | | | | |
| | DRB1*142301 | | | | | |
| | DRB1*142302 | | | | | |
| | DRB1*1424 | | | | | |
| | DRB1*1425 | | | | | |
| | DRB1*1426 | | | | | |
| | DRB1*1427 | | | | | |
| | DRB1*1428 | | | | | |
| | DRB1*1429 | | | | | |
| | DRB1*1430 | | | | | |
| | DRB1*1431 | | | | | |
| | DRB1*1432 | | | | | |
| | DRB1*1433 | | | | | |
| | DRB1*1434 | | | | | |
| | DRB1*1435 | | | | | |

Figure 4L

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*1436 | | | | | |
| | DRB1*1437 | | | | | |
| | DRB1*1438 | | | | | |
| | DRB1*1439 | | | | | |
| | DRB1*1440 | | | | | |
| | DRB1*1441 | | | | | |
| | DRB1*1442 | | | | | |
| | DRB1*1443 | | | | | |
| | DRB1*1444 | | | | | |
| | DRB1*1445 | | | | | |
| | DRB1*1446 | | | | | |
| | DRB1*1447 | | | | | |
| | DRB1*1448 | | | | | |
| | DRB1*1449 | | | | | |
| | DRB1*1450 | | | | | |
| | DRB1*1451 | | | | | |
| | DRB1*1452 | | | | | |
| | DRB1*1453 | | | | | |
| | DRB1*1454 | | | | | |
| | DRB1*1455 | | | | | |
| | DRB1*1456 | | | | | |
| | DRB1*1457 | | | | | |
| | DRB1*1458 | | | | | |
| | DRB1*1459 | | | | | |
| | DRB1*1460 | | | | | |
| | DRB1*1461 | | | | | |
| | DRB1*1462 | | | | | |
| | DRB1*1463 | | | | | |
| | DRB1*1464 | | | | | |
| | DRB1*150101 | | | | | |
| | DRB1*150102 | | | | | |
| | DRB1*150103 | | | | | |
| | DRB1*150104 | | | | | |
| | DRB1*150105 | | | | | |
| | DRB1*150106 | | | | | |
| | DRB1*150201 | | | | | |
| | DRB1*150202 | | | | | |

Figure 4M

| HLA-DRA | HLA-DRB1 | HLA-DRB2-9 | HLA-DQA1 | HLA-DQB1 | HLA-DPA1 | HLA-DPB1 |
|---|---|---|---|---|---|---|
| | DRB1*150203 | | | | | |
| | DRB1*150204 | | | | | |
| | DRB1*1503 | | | | | |
| | DRB1*1504 | | | | | |
| | DRB1*1505 | | | | | |
| | DRB1*1506 | | | | | |
| | DRB1*1507 | | | | | |
| | DRB1*1508 | | | | | |
| | DRB1*1509 | | | | | |
| | DRB1*1510 | | | | | |
| | DRB1*1511 | | | | | |
| | DRB1*1512 | | | | | |
| | DRB1*1513 | | | | | |
| | DRB1*1514 | | | | | |
| | DRB1*1515 | | | | | |
| | DRB1*1516 | | | | | |
| | DRB1*1517N | | | | | |
| | DRB1*1518 | | | | | |
| | DRB1*1519 | | | | | |
| | DRB1*1520 | | | | | |
| | DRB1*1521 | | | | | |
| | DRB1*1522 | | | | | |
| | DRB1*160101 | | | | | |
| | DRB1*160102 | | | | | |
| | DRB1*160201 | | | | | |
| | DRB1*160202 | | | | | |
| | DRB1*1603 | | | | | |
| | DRB1*1604 | | | | | |
| | DRB1*160501 | | | | | |
| | DRB1*160502 | | | | | |
| | DRB1*1607 | | | | | |
| | DRB1*1608 | | | | | |
| | DRB1*1609 | | | | | |
| | DRB1*1610 | | | | | |
| | DRB1*1611 | | | | | |

Figure 4N

| HLA-DMA | HLA-DMB | HLA-DOA | HLA-DOB |
|---|---|---|---|
| DMA*0101 | DMB*0101 | DOA*010101 | DOB*01010101 |
| DMA*0102 | DMB*0102 | DOA*01010201 | DOB*01010102 |
| DMA*0103 | DMB*0103 | DOA*01010202 | DOB*010102 |
| DMA*0104 | DMB*0104 | DOA*01010203 | DOB*010103 |
|  | DMB*0105 | DOA*010103 | DOB*010201 |
|  | DMB*0106 | DOA*01010401 | DOB*010202 |
|  | DMB*0107 | DOA*01010402 | DOB*0103 |
|  |  | DOA*010105 | DOB*01040101 |
|  |  | DOA*010106 | DOB*01040102 |
|  |  | DOA*0102 |  |
|  |  | DOA*0103 |  |
|  |  | DOA*0104N |  |

HLA HOMOZYGOUS CELLS

CROSS-REFERENCE

This application is a Continuation Application of U.S. patent application Ser. No. 12/044,471 filed Mar. 7, 2008, which claims the benefit under 35 U.S.C. §119(e) of U.S. Provisional Patent Application No. 60/905,966, filed Mar. 9, 2007, the content of which application is incorporated herein by reference in its entirety.

STATEMENT REGARDING FEDERALLY SPONSORED RESEARCH

The U.S. government may have certain rights in this invention, pursuant to grant nos. P20 GM69983 and R01 DK55759 awarded by the National Institutes of Health.

BACKGROUND

Transplantation of functional cells and tissues from a donor individual into a recipient is a major means of replacing failing or non-functional organs or tissues in the recipient. One of the major obstacles to successful transplantation is rejection of the transplanted cells or tissues by the recipient's immune system, due to tissue incompatibility. Immunosuppressive drugs such as cyclosporin A are currently used to reduce transplant rejection. However, immunosuppressive drugs are costly, toxic, and sometimes ineffectual. In humans, molecules encoded by the human leukocyte antigen (HLA) locus provide the context for the recognition of "non-self" or foreign cells by the transplant recipient.

The histocompatibility type of an individual is determined by many genes located in the HLA locus on human chromosome 6. Every person has two copies of the HLA locus—one on each copy of chromosome 6. There are several different versions or "haplotypes" of the genes in the HLA locus, and since there are two copies of each gene, it is very unlikely that two individuals have the same versions of each gene or "HLA type."

To ensure that transplants, such as bone marrow transplants, are not rejected by a recipient, attempts are made to use a donor with the same HLA type. The chances that a prospective recipient's sibling will have the same HLA type as the recipient are about 1 in 4. Therefore, siblings are usually used as donors when performing bone marrow transplantation. If no HLA-matched sibling is available, then an unrelated, HLA-matched, donor can sometimes be found; however, this requires searching through thousands of potential donors in the unrelated bone marrow donor registry to find an HLA match. More typically, where an unrelated donor is used, an exact match is not found; instead, a near-match is used.

In solid organ transplantation, HLA matching is typically not possible, due to the limited number of donors. Because organ transplantation typically involved HLA unmatched donors and recipients, aggressive immunosuppressive medications are typically required. These medications are very toxic and often fail to prevent transplant rejection.

There is an ongoing need in the art for HLA matched stem cells that can serve as donors in various therapeutic transplant settings.

Literature

U.S. Pat. No. 7,030,292; WO 98/48005; U.S. Pat. No. 6,986,887.

SUMMARY OF THE INVENTION

The present invention provides methods of generating a mammalian cell that is homozygous at a locus of interest, as well as cells made by the method. The present invention further provides methods of using the cells.

BRIEF DESCRIPTION OF THE DRAWINGS

FIG. 3 depicts Class I HLA alleles.

FIG. 4 depicts Class II HLA alleles.

DEFINITIONS

Figure 1:
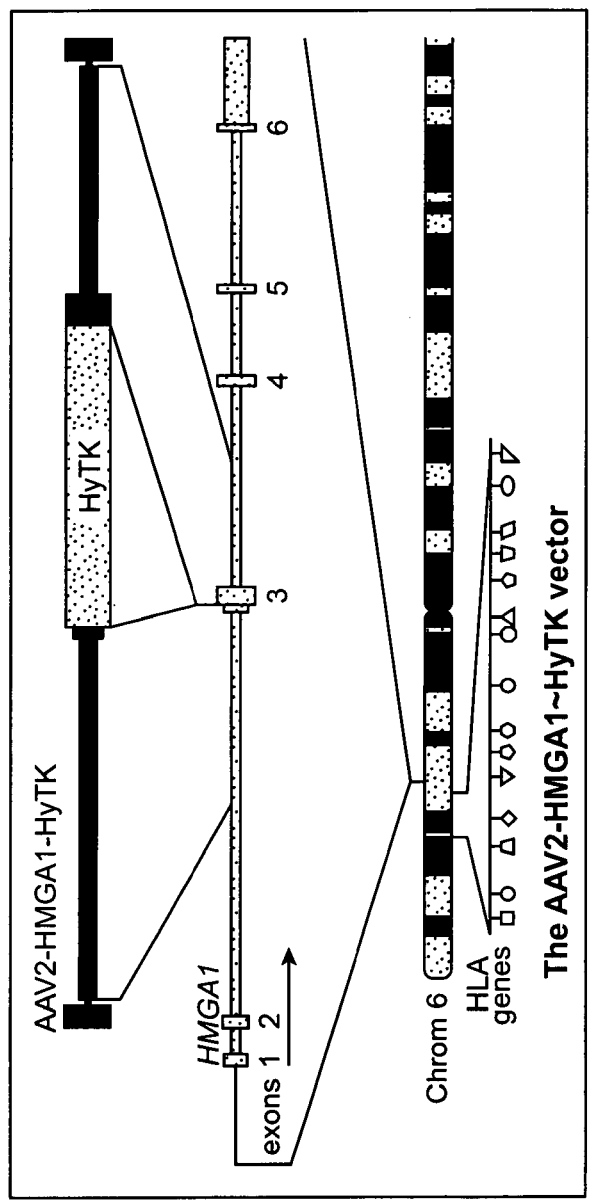
FIG. 1 is a schematic depiction of the AAV2-HMGA-1-HyTK vector.

As used herein, the term "stem cell" refers to an undifferentiated cell that can be induced to proliferate. The stem cell is capable of self-maintenance or self-renewal, meaning that with each cell division, one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type.

As used herein, the term "genetic modification" refers to a permanent or transient genetic change induced in the genome of a cell following introduction of new nucleic acid (i.e., DNA exogenous to the cell). Genetic modification can be accomplished by incorporation of the new ("exogenous") DNA into the genome of the host cell, or by transient or stable maintenance of the new DNA as an episomal element. Genetic modifications include, e.g., duplication of an endogenous nucleotide sequence in the nuclear genome. Following induction of a genetic change in the genome (e.g., the nuclear genome) of a cell, the exogenous DNA can remain in the cell (e.g., can be integrated into the genome, or can be present extrachromosomally), or can be absent from the cell (e.g., deleted from the genome). Means for effecting a "genetic modification" exclude parthenogenesis.

A "parvoviral vector" refers to a vector based on or derived from a parvovirus such as adeno-associated virus (AAV) and minute virus of mice (MVM). See, e.g., Hendrie et al. (2003) *J. Virol.* 77:13136-13145; and Russell et al. (2002) *Nat. Biotech.* 20:658.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes, but is not limited to, AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), and AAV type 8 (AAV-8).

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (LTRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virus or viral particle is one that comprises a polynucleotide component which it is capable of delivering into a cell for which the viral species is trophic. The term does not necessarily imply any replication capacity of the virus. Assays for counting infectious viral particles are described elsewhere in this disclosure and in the art. Viral infectivity can be expressed as the P:I ratio, or the ratio of total viral particles to infective viral particles.

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" means the amount of a compound or a number of cells that, when administered to a mammal or other subject for treating a disease, is sufficient to effect such treatment for the disease. The "therapeutically effective amount" will vary depending on one or more factors such as the cell, the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an HLA homozygous cell" includes a plurality of such cells and reference to "the rAAV vector" includes reference to one or more rAAV vectors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides cells that are genetically modified such that they are homozygous at a human leukocyte antigen (HLA) locus. These HLA homozygous cells are compatible with any recipient containing a single copy of that HLA locus present in the HLA homozygous cells, regardless of the other haplotype present in the recipient. Thus, only one HLA haplotype need be matched. The HLA homozygous cells can also be introduced into individuals who have an HLA haplotype that is not an exact match of the HLA haplotype in the HLA homozygous cell.

Figure 5:
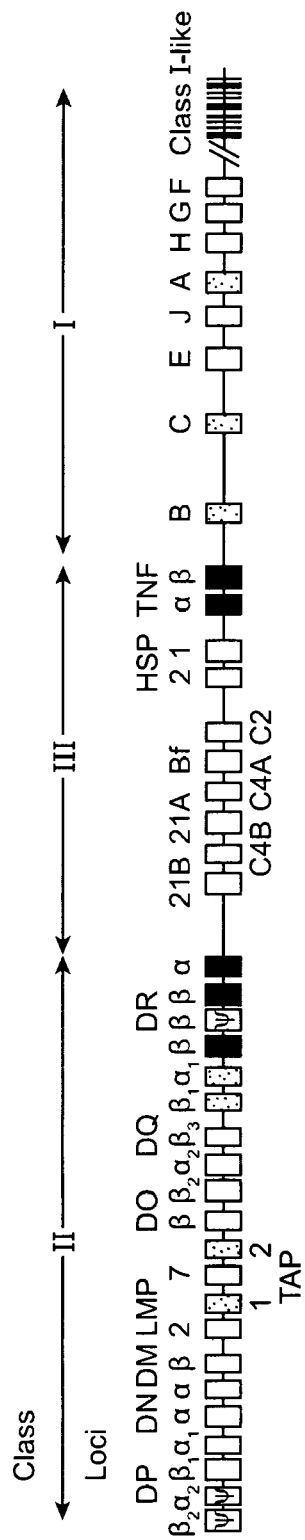
FIG. 5 is a schematic depiction of human HLA genes.
Figure 6:
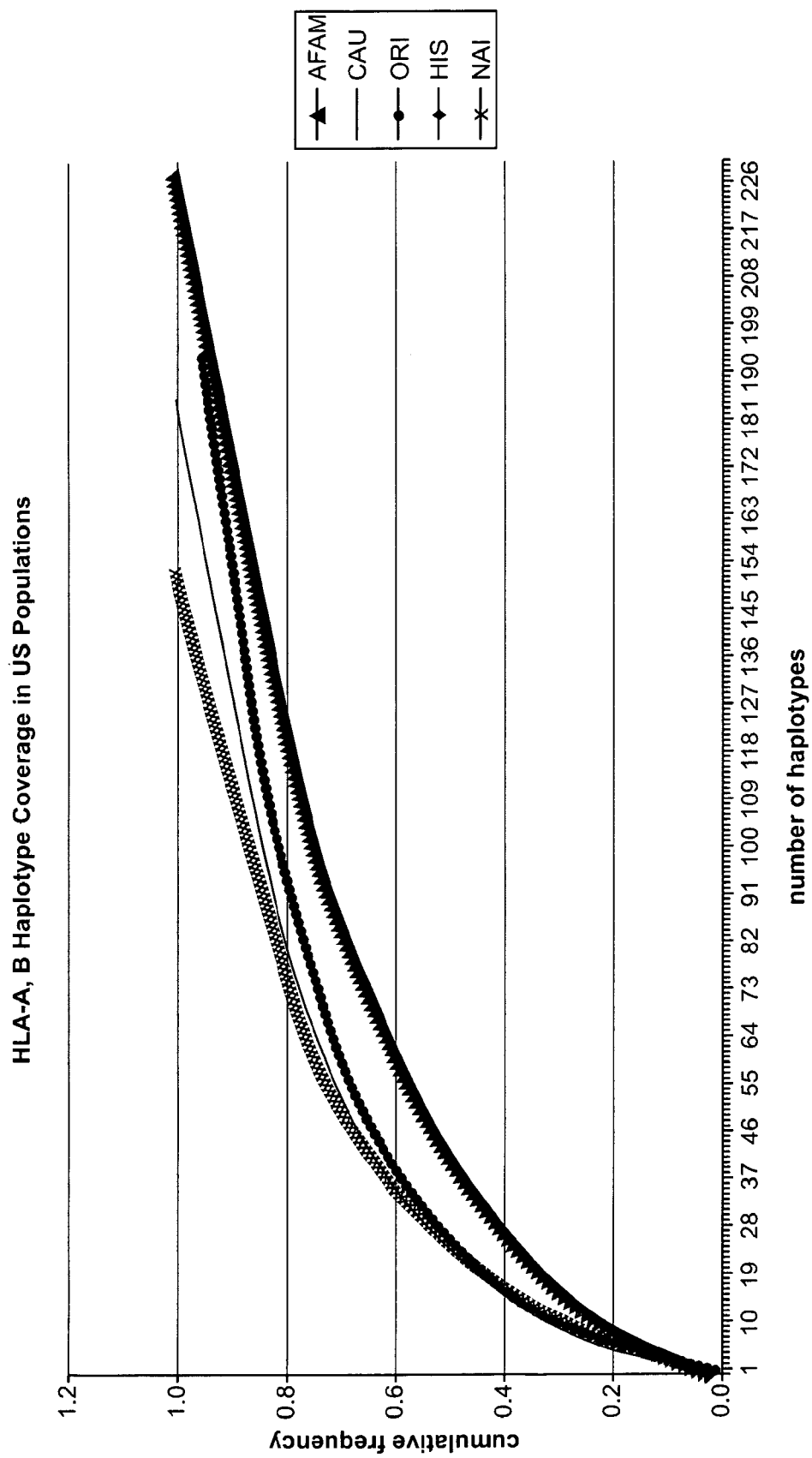
FIG. 6 is a graph depicting HLA-A,B coverage in U.S. populations.
Figure 7:
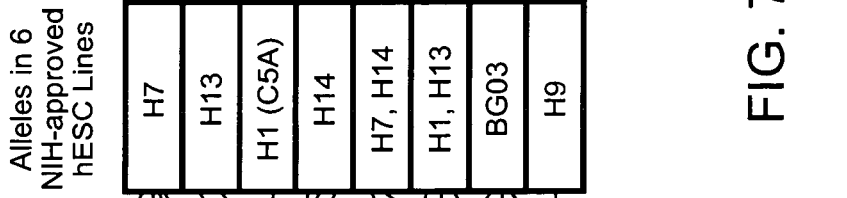
FIG. 7 depicts common HLA-A,B haplotypes in five U.S. populations.

An HLA haplotype is a collection of HLA class I and class II alleles found on a given chromosome in an individual. Currently known HLA class I and class II alleles are depicted in FIGS. 3 and 4, respectively. The human HLA locus is depicted schematically in FIG. 5. HLA-A,B haplotype coverage in U.S. populations is depicted in FIG. 6; and common HLA-A,B haplotypes in five U.S. populations are depicted in FIG. 7. For FIG. 7, see Faden et al. (2003) *Hastings Center Report* 33:13.

The present invention provides a repository (e.g., a library) of HLA homozygous cells. The HLA haplotypes represented in a subject library can reflect the most common HLA haplotypes found in human populations, e.g., common Caucasian HLA haplotypes, common HLA haplotypes found in individuals of African ancestry, common Asian HLA haplotypes, common Hispanic HLA haplotypes, common Native American HLA haplotypes, etc. For example, a single abundant haplotype can be present in a significant proportion of a population, allowing a single HLA homozygous cell line to serve as a histocompatible donor for a significant percent of patients. The library of cells can include HLA homozygous cells of the same type; HLA homozygous stem cells of the same cell type; HLA homozygous cells of two or more different cell types; etc.

The HLA homozygous cells described herein can find use in a broad array of clinical applications involving transplantation of cells and/or tissues. The HLA homozygous cells are HLA compatible with a recipient, and therefore can be introduced into the recipient without the need for immunosuppressive therapy, or at least with reduced need for immunosuppressive therapy. A standard immunosuppressive drug regimen costs thousands of dollars per month, and can have undesirable side effects, including infections and cancers that are often life-threatening and expensive to treat. The present HLA homozygous cells thus overcome some of the obstacles currently limiting the use of human cells for clinical applications.

Genetically Modified, HLA Homozygous Cells

The present invention provides genetically modified, HLA homozygous human cells. In some cases, the HLA homozygous cell is an HLA homozygous stem cell. In other cases, the HLA homozygous cell is a progenitor cell. In still other cases, the HLA homozygous cell is a terminally differentiated cell. The present invention also provides progeny of a subject HLA homozygous stem cell, including progeny that are differentiated. Thus, e.g., the present invention provides HLA homozygous cardiomyocytes; HLA homozygous differentiated progeny of a hematopoietic stem cell; HLA homozygous cartilage cells; HLA homozygous pancreatic islet cells; and the like.

Subject HLA homozygous cells are generated by genetic modification of an HLA heterozygous parent stem cell, using methods that are described in more detail below. Features of the parent HLA heterozygous cells are described below.

Parent HLA Heterozygous Cells

HLA heterozygous cells that are genetically modified to be HLA homozygous are referred to herein as "parent HLA heterozygous cells" or simply "parent cells." Parent cells that are can be genetically modified to generate a subject HLA homozygous cell include, but are not limited to, stem cells, e.g., hematopoietic stem cells, embryonic stem cells, mesenchymal stem cells, neural stem cells, epidermal stem cells, endothelial stem cells, gastrointestinal stem cells, liver stem cells, cord blood stem cells, amniotic fluid stem cells, pancreatic stem cells, and the like; as well as differentiated cells that can be cultured in vitro and used in a therapeutic regimen, where such cells include, but are not limited to, keratinocytes, adipocytes, cardiomyocytes, pancreatic islet cells, retinal cells, and the like. The parent cell that is used will depend in part on the nature of the disorder or condition to be treated.

Suitable parent human embryonic stem (ES) cells include, but are not limited to, any of a variety of available human ES lines, e.g., BG01(hESBGN-01), BG02 (hESBGN-02), BG03 (hESBGN-03) (BresaGen, Inc.; Athens, Ga.); SA01 (Sahlgrenska 1), SA02 (Sahlgrenska 2) (Cellartis AB; Goeteborg, Sweden); ES01 (HES-1), ES01 (HES-2), ES03 (HES-3), ES04 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA13 (H13), WA14 (H14) (Wisconsin Alumni Research Foundation; WARF; Madison, Wis.). Cell line designations are given as the National Institutes of Health (NIH) code, followed in parentheses by the provider code. See, e.g., U.S. Pat. No. 6,875,607.

Methods of culturing human ES cells are known in the art. See, e.g., U.S. Pat. No. 6,875,607. Human ES cells can be cultured in vitro using any known method.

Suitable parent human ES cell lines can be positive for one, two, three, four, five, six, or all seven of the following markers: stage-specific embryonic antigen-3 (SSEA-3); SSEA-4; TRA 1-60; TRA 1-81; Oct-4; GCTM-2; and alkaline phosphatase. Parent human ES cell lines can be negative for SSEA-1.

Hematopoietic stem cells (HSCs) are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining and culturing NSCs are known in the art.

Mesenchymal stem cells (MSC), originally derived from the embryonal mesoderm and isolated from adult bone marrow, can differentiate to form muscle, bone, cartilage, fat, marrow stroma, and tendon. Methods of isolating and culturing MSC are known in the art; and any known method can be used to obtain MSC. See, e.g., U.S. Pat. No. 5,736,396, which describes isolation and culture of human MSC.

Suitable parent cells can be euploid, e.g., have one of the following karyotypes: 46XY and 46XX. In some cases, parent cells are aneuploid.

Suitable parent cells include cells that are free of intracellular pathogens, e.g., do not have a detectable intracellular pathogen. For example, a suitable parent cell in which one or more intracellular pathogens cannot be detected. Example of such intracellular pathogens include, e.g., human papilloma virus (HPV), cytomegalovirus (CMV), Epstein-Barr virus (EBV), human immunodeficiency virus (HIV), herpes simplex virus (HSV), mycoplasma, rickettsia, replication-competent retroviruses, hepatitis A virus, hepatitis B virus, hepatitis C virus, and the like.

Suitable parent cells that do not include known deleterious mutations, where known deleterious mutations include, but are not limited to, deleterious mutations in a structural protein, and deleterious mutations in a functional protein, e.g., an enzyme, a transcription factor, a tumor suppressor; deleterious mutations in a non-coding region of a gene; loss of a coding region for a protein; mutations resulting in abnormal methylation patterns; and the like. Examples of known deleterious mutations include, but are not limited to, a mutation in cystic fibrosis transmembrane conductance regulator (CFTCR) that leads to cystic fibrosis (e.g., a ΔF508 mutation; a G542X mutation; a G551D mutation; an N1303K mutation; a W1282X; etc.); more than 40 CAG repeats in the huntingtin gene; a mutation in the adenosine deaminase gene; a mutation in XMR1, e.g., CGG repeats in the 5' untranslated region of the FMR1 gene; mutations in the p53 tumor suppressor gene; mutations in Ras; mutations in type I collagen genes COL1A1 and COL1A2 that cause osteogenesis imperfecta; globlin mutations that case sickle cell anemia or thalassemia; mutations in clotting factor genes that cause hemophilia; mutations in dystrophin that cause muscular dystrophy; and the like.

Suitable parent cells also include cells that do not have any gross chromosomal abnormalities that can be detected by karyotyping, e.g., aneuploidy of any chromosome, e.g., chromosome 21 trisomy, chromosome 18 trisomy; deletions of a segment of a chromosome; inversion of a segment of a chromosome; duplication of a segment of a chromosome; loss of a portion of a chromatid arm; translocation of all or a part of a chromosome to another chromosome; and the like.

Before genetically modifying a parent HLA heterozygous cell such that it is HLA homozygous, the parent cell can be manipulated in any of a number of ways (e.g., by genetic modification, selection, etc.), as described below.

An HLA heterozygous parent cell can be genetically modified before being genetically modified to become HLA homozygous. For example, an HLA heterozygous parent cell can be genetically modified with a nucleic acid that comprises a nucleotide sequence encoding a therapeutic protein, such that the therapeutic protein is produced by the cell (e.g, in a constitutive or an inducible manner). Non-limiting examples of suitable therapeutic proteins include, but are not limited to, cytokines; lymphokines; erythropoietin; colony stimulating factors; growth factors; an interleukin; clotting factors; glucose level regulating proteins (e.g., insulin); growth hormones; tumoricidal proteins; anti-angiogenic proteins; and the like.

As another example, a deleterious mutation in a parent HLA heterozygous cell can be corrected before making the cell HLA homozygous. Any known method can be used to correct a deleterious mutation. See, e.g., WO 98/48005; Inoue et al. (2001) *Mol. Ther.* 3:526-530; and Miller et al. (2006) *Nat. Biotech.* 24:1022. Where an HLA heterozygous parent cell has DNA encoding transposons or viral remnants in its nuclear genome, such DNA can be removed. Furthermore, a parent cell can be genetically modified with one or more suicide genes that could be activated to as to kill a transplanted cell.

Genetically Modified HLA Homozygous Cells

A subject HLA homozygous cell is homozygous for an HLA haplotype that is compatible with at least one prospective recipient. A subject HLA homozygous cell can be homozygous for an HLA haplotype that is found in from about 0.01% to about 25% or more of a selected human population. For example, a subject HLA homozygous cell can be homozygous for an HLA haplotype found in from about 0.01% to about 25% or more of a Caucasian population, an Asian population (e.g., Chinese, Japanese, Taiwanese, Korean, etc.), an African-American population, an Hispanic population, etc.

Currently known HLA class I and class II alleles are depicted in FIGS. 3 and 4, respectively. The human HLA locus is depicted schematically in FIG. 5. An HLA haplotype is a collection of HLA class I and class II alleles found on a given chromosome in an individual. A subject HLA homozygous cell or progeny thereof, is homozygous for the entire HLA locus, including class I and class II HLA molecule-encoding portions of the locus. HLA-A,B haplotype coverage in U.S. populations is depicted in FIG. 6. Common HLA-A,B haplotypes in five U.S. populations are depicted in FIG. 7, where the following abbreviations are used: AFAM, African American; CAU, Caucasian; ORI, Oriental (e.g., Asian): HIS, Hispanic; and NAI, Native American Indian. See, e.g., Cao et al. (2001) *Human Immunol.* 62:1009. A subject HLA homozygous cell can include one of the common HLA-A,B haplotypes depicted in FIG. 7.

As described in more detail below, a subject HLA homozygous cell can be generated in a process that involves genetic modification of a parent stem cell with a recombinant targeting parvoviral vector, followed by negative selection to select for loss of the negative selection marker. Negative selection results in loss of the negative selection marker and the entire recombinant parvoviral vector, such that a subject HLA homozygous cell does not contain any detectable parvoviral sequences from the recombinant parvoviral vector that integrated into the genome during the positive selection step.

As noted above, a parent cell that is HLA heterozygous (i.e., heterozygous at the HLA locus) is genetically modified such that it is homozygous at the HLA locus, generating a genetically modified HLA homozygous cell. A subject HLA homozygous cell can be homozygous at one or more loci other than the HLA locus; however, a majority of the non-HLA loci in a subject HLA homozygous cells are heterozygous. For example, a subject HLA homozygous cell comprises a genome in which at least about 50%, at least about 75%, at least about 80%, at least about 85%, at least about 90%, at least about 95%, at least about 98%, or at least about 99%, or more (e.g., 99.5%, 99.9%, etc.), of the loci other than the HLA locus are heterozygous.

As noted above, a parent cell can be substantially free of one or more intracellular pathogens, e.g., no detectable intracellular pathogen is present in a parent stem cell. Similarly, a subject HLA homozygous cell can be substantially free of intracellular pathogens. Thus, e.g., a subject HLA homozygous cell can have no detectable intracellular pathogen, where intracellular pathogens include, e.g., HPC, EBV, CMV, HIV, HSV, HCV, HBV, HAV, mycoplasma, and the like. Whether a subject HLA homozygous cell is free of one or more intracellular pathogens is readily determined using any of a variety of methods, including, e.g., polymerase chain reaction (PCR) analysis of genomic DNA using primers specific for a particular pathogen (e.g., where pathogen nucleic acid is genomically integrated); and the like.

A parent stem cell generally does not have any detectable gross chromosomal abnormalities, e.g., chromosomal abnormalities that can be detected by karyotype. Similarly, subject HLA homozygous cell does not have any detectable gross chromosomal abnormalities that can be detected by karyotyping, e.g., aneuploidy of any chromosome, e.g., chromosome 21 trisomy, chromosome 18 trisomy; deletions of a segment of a chromosome; inversion of a segment of a chromosome; duplication of a segment of a chromosome; loss of a portion of a chromatid arm; translocation of all or a part of a chromosome to another chromosome; and the like. An HLA homozygous cell can be euploid or aneuploid. In some cases, an HLA homozygous cell is euploid.

Analysis of the nuclear chromosomal karyotype can be used to assess genetic stability of an HLA homozygous cell or progeny thereof. For example, an HLA homozygous cell that is maintained in culture for an extended period of time can be periodically subjected to analysis of the nuclear chromosomal karyotype to determine whether any gross chromosomal abnormalities are present and detectable.

A parent cell can be one that lacks one or more known deleterious mutations. Similarly, a subject HLA homozygous can lack one or more known deleterious mutations, where known deleterious mutations include, but are not limited to, deleterious mutations in a structural protein, and deleterious mutations in a functional protein, e.g., an enzyme, a transcription factor, a tumor suppressor; deleterious mutations in a non-coding region of a gene; loss of a coding region for a protein; mutations resulting in abnormal methylation patterns; and the like.

Whether a subject HLA homozygous cell or progeny thereof contains any deleterious mutations can be readily determined using DNA microarray analysis, proteomic analysis, or other method for detecting the presence of a mutation.

Furthermore, a subject HLA homozygous cell can be one that does not undergo uncontrolled cell proliferation, i.e., is not tumorigenic.

Further Genetic Modifications

A subject HLA homozygous cell can be further genetically modified, depending on various factors, including the therapeutic purpose for which the HLA homozygous cell is intended.

For example, an HLA homozygous cell can be genetically modified to include a nucleic acid comprising a nucleotide sequence encoding a therapeutic polypeptide, e.g., a polypeptide that is need by the host and that the host does not produce; a polypeptide that the host produces, but in insufficient quantities; and a functional version of a mutant, non-functional polypeptide that the host produces. Non-limiting examples of such therapeutic proteins include, but are not limited to, cytokines; lymphokines; erythropoietin; colony stimulating factors; growth factors; an interleukin; clotting factors; glucose level regulating proteins (e.g., insulin); growth hormones; and the like.

Selection for Differentiated Cell Types

Depending on the therapeutic application in which a subject HLA homozygous cell is to be used, the HLA homozygous cell can be manipulated in in vitro culture. For example, a subject HLA homozygous stem cell or progenitor cell can be induced in vitro to differentiate into a desired cell type. Where a particular cell type is desired, an HLA homozygous stem cell is cultured under conditions that provide for differentiation into the cell type. Cells that have differentiated into a desired cell type are readily identified by the presence of one or more cell markers that are indicators of the cell type. The present invention provides differentiated HLA homozygous cells, e.g., HLA homozygous cardiomyocytes, HLA homozygous neurons, HLA homozygous glial cells, HLA homozygous mesenchymal lineage cells, HLA homozygous pancreatic islet cells, etc.

Methods of inducing a stem cell to undergo differentiation in vitro are known in the art; and any known method can be used. See, e.g., Odorico et al. ((2001) Stem Cells 19:193-204).

A subject method can involve: a) inducing differentiation in a population of HLA homozygous stem cells, generating a mixed cell population that includes undifferentiated stem cells and differentiated cells; and b) separating the differentiated cells from the undifferentiated cells. As an example, a subject method can involve: a) inducing cardiomyogenesis in a population of HLA homozygous stem cells, generating a mixed population of undifferentiated stem cells and cardiomyocytes; and b) separating cardiomyocytes from the undifferentiated (non-cardiomyocyte) cells. The separation step can involve contacting the mixed cell population with an antibody specific for a cardiomyocyte-specific cell surface marker.

Neuronal Cells and Glial Cells

For example, under certain in vitro culture conditions, a stem cell can be induced to differentiate into a neuronal cell, an astrocyte, an oligodendrocyte, or a neuronal precursor cell. As an example, an HLA homozygous cell can be cultured in the presence of ligands that bind growth factor receptors to promote enrichment for neural precursor cells. The growth environment may contain a neural cell supportive extracellular matrix, such as fibronectin. Other methods for inducing differentiation of an ES cell into a neuronal precursor cell are described in, e.g., U.S. Pat. Nos. 6,887,706; and 7,011,828. Markers of interest include, but are not limited to, β-tubulin III or microtubule-associated protein 2 (MAP-2), characteristic of neurons; glial fibrillary acidic protein (GFAP), present in astrocytes; galactocerebroside (GalC) or myelin basic protein (MBP); characteristic of oligodendrocytes; Nestin or Musashi, characteristic of neural precursors and other cells. A mature neuronal cell can be characterized by an ability to express one, two, three, four, five, six, seven, or all eight of: 160 kDa neuro-filament protein, MAP2ab, glutamate, synaptophysin, glutamic acid decarboxylase (GAD), tyrosine hydroxylase, GABA, and serotonin. The differentiated cells forming neural progenitor cells, neuron cells and/or glial cells can also be characterized by expressed markers characteristic of differentiating cells. The in vitro differentiated cell culture can be identified by detecting molecules such as markers of the neuroectodermal lineage, markers of neural progenitor cells, neuro-filament proteins, MAP2ab, glutamate, synaptophysin, glutamic acid decarboxylase, GABA, serotonin, tyrosine hydroxylase, β-tubulin, β-tubulin III, GABA Aα2 receptor, glial fibrillary acidic protein (GFAP), 2', 3'-cyclic nucleotide 3'-phosphodiesterase (CNPase), plp, DM-20, O4, and NG-2 staining.

Hepatocytes

As another example, an HLA homozygous stem cell can be cultured in the presence of a hepatocyte differentiation agent to promote enrichment for hepatocyte-like cells. The growth environment may contain a hepatocyte supportive extracellular matrix, such as collagen or Matrigel™. Suitable differentiation agents include various isomers of butyrate and their analogs, exemplified by n-butyrate. The cultured cells are optionally cultured simultaneously or sequentially with a hepatocyte maturation factor, such as an organic solvent like dimethyl sulfoxide (DMSO); a maturation cofactor such as retinoic acid; or a cytokine or hormone such as a glucocorticoid, epidermal growth factor (EGF), insulin, transforming growth factors (TGF-α and TGF-β), fibroblast growth factors (FGF), heparin, hepatocyte growth factors (HGF), interleukins (IL-1 and IL-6), insulin-like growth factors (IGF-I and IGF-II), and heparin-binding growth factors (HBGF-1). Hepatocyte lineage cells differentiated from stem cells can display one, two, three, or more, of the following markers: $α_1$-antitrypsin (AAT) synthesis, albumin synthesis, asialoglycoprotein receptor (ASGR) expression, absence of α-fetoprotein, evidence of glycogen storage, evidence of cytochrome p450 activity, and evidence of glucose-6-phosphatase activity.

Cardiomyocytes

An HLA homozygous stem cell can be induced in vitro to differentiate into a cardiomyocyte, generating an HLA homozygous cardiomyocyte. An HLA homozygous cardiomyocyte can be used to treat, e.g., areas of ischemic cardiac tissue resulting from myocardial infarction; heart failure; and the like. Suitable cardiomyocyte-specific cell surface markers include, but are not limited to, troponin and tropomyosin.

Mesenchymal Lineages

An HLA homozygous stem cell can be induced in vitro to differentiate into a cell of a mesenchymal lineage, e.g., a lineage selected from osteogenic, chondrogenic, tendonogenic, ligamentogenic, myogenic, marrow stromagenic, adipogenic and dermogenic. Thus, e.g., an HLA homozygous mesenchymal stem cell can be induced in vitro to differentiate into an osteoblast, a chondrocyte, a myoblast, a stromal cell, etc., using any known method. See, e.g., U.S. Pat. No. 5,736,396, which describes methods for in vitro differentiation of human mesenchymal stem cells.

Pancreatic Islet Cells

An HLA homozygous stem cell can be induced in vitro to differentiate into a pancreatic islet cell, generating an HLA homozygous pancreatic islet cell, which can be used to treat Type 1 diabetes. Methods of inducing differentiation into a pancreatic islet cell are described in, e.g., Zulewski (2006) *Swiss Med. Weekly* 136(41-42):647-54; Trounson (2006) *Endocrin. Rev.* 27(2):208-19; Soria et al. (2005) *Novartis Found. Symp.* 265:158-67; and Xu et al. (2006) *Cloning and Stem Cells* 8:96-107.

Separation of Differentiated Cells from Undifferentiated Cells

As noted above, where a population of HLA homozygous stem cells is induced in vitro to differentiate, a mixed cell population can result, where the mixed cell population includes undifferentiated HLA homozygous cells and differentiated HLA homozygous cells. Where it is desired to generate a population of HLA homozygous cells in which most or substantially all of the cells are HLA homozygous differentiated cells, the differentiated cells can be separated from the undifferentiated cells. Separation can be carried out on the basis of cell surface markers expressed by differentiated cells, but not by undifferentiated cells. Suitable cell surface markers for differentiated cells of various cell types are known in the art, and are described above.

Separation can be carried out using well-known methods, including, e.g., any of a variety of sorting methods, e.g., fluorescence activated cell sorting (FACS), negative selection methods, etc. The selected (differentiated) cells are separated from non-selected (undifferentiated) cells, generating a population of selected ("sorted") cells. A selected cell population can be at least about 75%, at least about 80%, at least about 85%, at least about 90%, at least about 95%, at least about 98%, at least about 99%, or greater than 99% differentiated cells of a particular (selected) cell type.

Cell sorting (separation) methods are well known in the art. Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide [PI], LDS). Any technique may be employed which is not unduly detrimental to the viability of the selected cells. Where the selection involves use of one or more antibodies, the antibodies can be conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry.

Compositions Comprising HLA Homozygous Cells or Progeny

Also provided are compositions, including pharmaceutical compositions, comprising a subject HLA homozygous cell, or a progeny of such a cell, including, e.g., a differentiated progeny of an HLA homozygous stem cell or progenitor cell. A subject cell composition comprises an HLA homozygous cell (e.g., an HLA homozygous stem cell, or a progeny thereof) and one or more additional components. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

For administration to a mammalian host, a subject HLA homozygous cell can be formulated as a pharmaceutical composition, where a pharmaceutical composition comprises, in addition to a subject homozygous cell, at least one pharmaceutically acceptable excipient. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical composition can be a sterile aqueous or non-aqueous solution, suspension or emulsion, which additionally comprises a physiologically acceptable carrier (i.e., a non-toxic material that does not substantially adversely affect cell viability or activity). Any suitable carrier known to those of ordinary skill in the art may be employed in a subject pharmaceutical composition. The selection of a carrier will depend, in part, on the nature of the cells being administered. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition can additionally contain preservatives and/or other additives such as, for example, antimicrobial agents, anti-oxidants, chelating agents and/or inert gases, and/or other active ingredients.

A subject HLA homozygous cell or progeny thereof can be encapsulated, according to known encapsulation technologies, including microencapsulation (see, e.g., U.S. Pat. Nos. 4,352,883; 4,353,888; and 5,084,350). Where a subject HLA homozygous stem cell or progeny thereof is encapsulated, the HLA homozygous stem cell or progeny thereof can be encapsulated by macroencapsulation, as described in U.S. Pat. Nos. 5,284,761; 5,158,881; 4,976,859; 4,968,733; 5,800,828 and published PCT patent application WO 95/05452.

A subject HLA homozygous stem cell or progeny thereof can be present in a matrix. The term "matrix" refers to any suitable carrier material to which the cells are able to attach themselves or adhere in order to form a corresponding cell composite, e.g., artificial tissue. In some embodiments, the matrix or carrier material, respectively, is present already in a three-dimensional form desired for later application. For example, bovine pericardial tissue is used as matrix which is crosslinked with collagen, decellularized and photofixed.

As an example, a matrix (also referred to as a "biocompatible substrate") is a material that is suitable for implantation into a subject onto which a cell population can be deposited. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate provides the supportive framework that allows cells to attach to it, and grow on it. Cultured populations of cells can then be grown on the biocompatible substrate, which provides the appropriate interstitial distances required for cell-cell interaction.

A subject HLA homozygous cell or progeny thereof can be cryopreserved according to routine procedures. For example, cryopreservation can be carried out on from about one to ten million cells in "freeze" medium which can include a suitable proliferation medium, 10% serum albumin (e.g., human serum albumin) and 7.5% dimethylsulfoxide. Cells are centrifuged. Growth medium is aspirated and replaced with freeze medium. Cells are resuspended as spheres. Cells are slowly frozen, by, e.g., placing in a container at −80° C. Cells are thawed by swirling in a 37° C. bath, resuspended in fresh culture medium.

Where desired, the differentiated cells can be formed into a tissue sheet, for use in transplantation into a recipient. A tissue sheet comprising, e.g., living HLA homozygous, differentiated cells and extracellular matrix is formed using any known method. See, e.g., U.S. Pat. No. 7,166,464.

HLA Homozygous Cell Library

As discussed above, a library of HLA homozygous cells is provided. A library includes one, two, three, four, five, six, seven, eight, nine, 10, 10-15, 15-20, 20-25, 25-30, or more than 30 different types of HLA homozygous cells. A subject library can include a first HLA homozygous cell homozygous for a first HLA haplotype; and at least a second HLA homozygous cell homozygous for a second HLA haplotype.

For example, a subject library can include a first HLA homozygous cell homozygous for a first HLA haplotype; a second HLA homozygous cell homozygous for a second HLA haplotype; a third HLA homozygous cell homozygous for a third HLA haplotype; a fourth HLA homozygous cell homozygous for a fourth HLA haplotype; and so on.

The different HLA haplotypes represented in a subject library can represent major HLA haplotypes found in various human populations, e.g., one or more major HLA haplotypes found in a Caucasian population; one or more major HLA haplotypes found in an African-American population; one or more major HLA haplotypes found in a Chinese population; one or more major HLA haplotypes found in a Japanese population; one or more major HLA haplotypes found in an Hispanic population; and the like.

A subject library can include a single cell type or can include two or more different cell types.

For example, a subject library can be a library of HLA homozygous cells, where all of the cells are of the same cell type. For example, a subject library can include a first HLA homozygous cardiomyocyte homozygous for a first HLA haplotype; a second HLA homozygous cardiomyocyte homozygous for a second HLA haplotype; a third HLA homozygous cardiomyocyte homozygous for a third HLA haplotype; a fourth HLA homozygous cardiomyocyte homozygous for a fourth HLA haplotype; and so on.

Alternatively, a subject library can include two or more different cell types. For example, the library can include a pancreatic islet cell, a cardiomyocyte, a keratinocyte, etc., where all of the cells are homozygous for the same HLA haplotype. In some cases, a subject library will include two or more sub-libraries, e.g., the library can include a sub-library of HLA homozygous pancreatic islet cells, including, e.g., a first HLA homozygous pancreatic islet cell of a first HLA haplotype, a second HLA homozygous pancreatic islet cell of a second HLA haplotype, etc.; a sub-library of HLA homozygous cardiomyocytes, including, e.g., a first HLA homozygous cardiomyocyte of a first HLA haplotype, a second HLA homozygous cardiomyocyte of a second HLA haplotype, etc.; a sub-library of keratinocytes; and so on.

In some embodiments, a subject library is a library of HLA homozygous stem cells. For example, a subject library can include a first HLA homozygous stem cell homozygous for a first HLA haplotype; a second HLA homozygous stem cell homozygous for a second HLA haplotype; a third HLA homozygous stem cell homozygous for a third HLA haplotype; a fourth HLA homozygous stem cell homozygous for a fourth HLA haplotype; and so on.

A subject library can be catalogued, e.g., by a searchable computer database, in which information regarding the HLA haplotype, and optionally additional information such as cell surface markers, karyotype information, and the like, is stored and can be searched.

Methods of Generating an HLA Homozygous Cell

The present invention further provides methods of generating an HLA homozygous cell or progeny thereof, including differentiated progeny. The methods generally involve genetically modifying an HLA heterozygous parent cell with a targeting vector comprising: a) a targeting nucleotide sequence that provides for homologous recombination with a target nucleotide sequence centromeric to a HLA locus on a first copy of chromosome 6 in the parent stem cell; b) a selectable marker(s) that provides for selection for integration of the targeting nucleotide sequence into the chromosome, and for selection for homozygosity at the HLA locus, where the selectable marker can be located within the targeting nucleotide sequence, to generate a genetically modified parent cell that includes the targeting sequence integrated into a first copy of chromosome 6 at a site centromeric to the HLA locus.

Selection of the genetically modified cell is then carried out. The above-described genetic modification can result in a mixed population of cells, where a proportion of the cells include the targeting sequence integrated into a first copy of chromosome 6 at a site centromeric to the HLA locus. Selection of cells that include the targeting sequence integrated into a first copy of chromosome 6 at a site centromeric to the HLA locus is carried out. Genetically modified parent cells that include the targeting sequence integrated into a first copy of chromosome 6 at a site centromeric to the HLA locus are then selected for duplication of one copy of the HLA locus in such a manner that both copies of chromosome 6 have the same HLA haplotype.

Any of a number of targeting vectors can be used. Parvoviral vectors are exemplified below. However, the method is not limited to use of a parvoviral targeting vector.

As noted above, a subject method can be carried out using a parvoviral targeting vector. In this case, the methods generally involve genetically modifying an HLA heterozygous parent cell with a parvoviral vector comprising: a) a targeting nucleotide sequence that provides for homologous recombination with a target nucleotide sequence centromeric to a HLA locus on a first copy of chromosome 6 in the parent cell; b) a selectable marker(s) that provides for selection for integration of the targeting nucleotide sequence into the chromosome, and for selection for homozygosity at the HLA locus, where the selectable marker(s) is located within the targeting nucleotide sequence; and c) at least one inverted terminal repeat, or a functional equivalent thereof, flanking the targeting nucleotide sequence, to generate a genetically modified parent cell. Selection steps are carried out as described above.

In some cases, both positive and negative selection in used. In these cases, the methods involve genetically modifying an HLA heterozygous parent cell with a parvoviral vector comprising: a) a targeting nucleotide sequence that provides for homologous recombination with a target nucleotide sequence centromeric to a HLA locus on a first copy of chromosome 6 in the parent cell; b) a selectable marker(s) that provides for positive and negative selection, where the selectable marker is located within the targeting nucleotide sequence; and c) at least one inverted terminal repeat, or a functional equivalent thereof, flanking the targeting nucleotide sequence, to generate a genetically modified parent cell.

The genetically modified stem cell is cultured under conditions that provide for positive selection and negative selection of the selectable marker. Positive selection results in a genetically modified parent stem cell comprising the parvoviral vector integrated into the target nucleotide sequence on the first copy of chromosome 6 at a location centromeric to the HLA locus. Negative selection results in a genetically modified stem cell that is homozygous for the HLA haplotype present on the second copy of chromosome 6. Negative selection also results in loss of the HLA locus and the parvoviral vector present on the first copy of chromosome 6.

Positive selection is carried out first, generating a genetically modified parent stem cell comprising the parvoviral vector integrated into the target nucleotide sequence on the first copy of chromosome 6 at a location centromeric to the HLA locus. Negative selection can be carried out following positive selection, e.g., negative selection can be carried out directly following the completion of positive selection. Alternatively, the genetically modified parent cell comprising the recombinant parvoviral vector integrated into the target nucleotide sequence on the first copy of chromosome 6 at a location centromeric to the HLA locus can be stored (e.g., cryopreserved); and negative selection can be performed at a later time (e.g., one day, two days to one week, one week to one month, one month to six months, or six months to one year, or later, following positive selection).

Modification of Other Loci

Described above are methods of generating a cell that is homozygous at the HLA locus. While the methods focus on the HLA locus, the same method can be applied to other loci, e.g., to generate a cell that is homozygous at a locus of interest. The present invention thus provides methods of generating a cell that is homozygous at a locus of interest; as well as cells generated by the method. The methods generally involve genetically modifying a parent cell that is heterozygous at a locus of interest with a targeting vector comprising: a) a targeting nucleotide sequence that provides for homologous recombination with a target nucleotide sequence centromeric to the locus of interest on a first copy of a chromosome in the parent stem cell; b) a selectable marker(s) that provides for selection for integration of the targeting nucleotide sequence into the first copy of the chromosome, where the selectable marker can be located within the targeting nucleotide sequence, to generate a genetically modified parent cell that includes the targeting sequence integrated into a first copy of the chromosome at a site centromeric to the locus of interest. Selection steps are carried out as described above, to generate a genetically modified cell that is homozygous at the locus of interest.

Recombinant Parvoviral Vector and Virion

The present invention also provides a recombinant targeting parvoviral vector (e.g., a recombinant targeting MVM vector; a recombinant targeting AAV vector) comprising: a) a targeting nucleotide sequence that provides for homologous recombination with a target nucleotide sequence centromeric to a histocompatibility locus; b) a selectable marker that provides for positive and negative selection, wherein the selectable marker is located within the targeting nucleotide sequence; and c) at least one inverted terminal repeat, or a functional equivalent thereof, flanking the targeting nucleotide sequence. The present invention also provides rAAV virions generated using a subject rAAV, where the rAAV virions are suitable for infecting a parent, HLA heterozygous, stem cell.

As noted above, the recombinant parvoviral vector that is used to generate a subject HLA homozygous stem cell includes: a) a targeting nucleotide sequence that provides for homologous recombination with a target nucleotide sequence centromeric to a HLA locus on a first copy of chromosome 6 in a parent stem cell; b) a selectable marker(s) that provides for positive and negative selection, where the selectable marker is located within the targeting nucleotide sequence; and c) at least one inverted terminal repeat, or a functional equivalent thereof, flanking the targeting nucleotide sequence.

The target nucleotide sequence can be any sequence present between the HLA locus and the centromere. As one non-limiting example, the target nucleotide sequence is a nucleotide sequence present in the HMGA1 gene. For example, the target nucleotide sequence can include HMGA1 exon 3 nucleotide sequences.

Selectable markers suitable for positive selection include, but are not limited to, nucleic acids comprising nucleotide sequences encoding a polypeptide that provides resistance to antimicrobial agents. Suitable selectable markers that provide for positive selection include, but are not limited to, a hygromycin B resistance gene (encoding aminoglycoside phosphotranferase (APH)) that confers resistance to hygromycin; a neomycin phosphotranferase gene (encoding neomycin phosphotransferase) that confers resistance to G418; pac, which confers resistance to puromycin; a zeomycin resistance gene, which confers resistance to zeomycin; a BlaS gene conferring blasticidin resistance; and the like.

Selectable markers suitable for negative selection include, but are not limited to, nucleic acids comprising nucleotide sequences encoding thymidine kinase, which confers sensitivity to gancyclovir.

A nucleic acid comprising a nucleotide sequence encoding a fusion protein that provides for both positive and negative can also be included in the parvoviral vector. For example, a fusion polypeptide comprising a hygromycin resistance portion and a thymidine kinase portion can be used. See, e.g., Lupton et al. (1991) *Mol. Cell Biol.* 11:3374-3378. As another example, a fusion polypeptide comprising a blasticidin resistance portion and a thymidine kinase portion can be used. See, e.g., Karreman (1998) *Nucl. Acids Res.* 26:2508-2510.

As noted above, the selectable marker(s) are located within the targeting sequence. The total combined length of the targeting sequence and selectable marker(s) is generally less than about 5 kilobases (kb).

The parvoviral vector includes at least one inverted terminal repeat, or a functional equivalent thereof, flanking the targeting nucleotide sequence. The nucleotide sequences of AAV UR regions are known. See, e.g., Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell. ITRs allow replication of the vector sequence in the presence of an appropriate mixture of Rep proteins. ITRs also allow for the incorporation of the vector sequence into the capsid to generate an AAV particle.

Genetically Modified Parent Cells Comprising Integrated Recombinant Parvoviral Vector As noted above, positive selection of a genetically modified parent cell results in a genetically modified parent cell comprising the targeting vector integrated into the target nucleotide sequence on the first copy of chromosome 6 at a location centromeric to the HLA locus. The present invention also provides a genetically modified parent cell comprising the targeting vector integrated into the target nucleotide sequence on the first copy of chromosome 6 at a location centromeric to the HLA locus. The genetically modified parent cell comprising the targeting vector integrated into the target nucleotide sequence on the first copy of chromosome 6 at a location centromeric to the HLA locus can be stored (e.g., cryopreserved) and kept for days, weeks, months, or years.

Generating an rAAV Virion

As noted above, the recombinant parvoviral vector can be a recombinant AAV (rAAV) vector. Methods of generating a recombinant AAV (rAAV) vector for use in a subject method are described in, e.g., Hirata and Russell (2000) *J. Virol.* 74:4612-4620. By way of introduction, it is typical to employ a host or "producer" cell for rAAV vector replication and packaging. Such a producer cell (usually a mammalian host cell) generally comprises or is modified to comprise several different types of components for rAAV production. The first component is a recombinant adeno-associated viral (rAAV) vector genome (or "rAAV pro-vector") that can be replicated and packaged into vector particles by the host packaging cell. The rAAV pro-vector will normally comprise a heterologous polynucleotide (or "transgene"), with which it is desired to genetically alter another cell. The transgene is generally flanked by one or two AAV inverted terminal repeats (ITRs) which comprise sequences that are recognized during excision, replication and packaging of the AAV vector, as well as during integration of the vector into a host cell genome.

A second component is a helper virus that can provide helper functions for AAV replication. Although adenovirus is commonly employed, other helper viruses can also be used as is known in the art. Alternatively, the requisite helper virus functions can be isolated genetically from a helper virus and the encoding genes can be used to provide helper virus functions in trans. The AAV vector elements and the helper virus (or helper virus functions) can be introduced into the host cell either simultaneously or sequentially in any order.

The final components for AAV production to be provided in the producer cell are "AAV packaging genes" such as AAV rep and cap genes that provide replication and encapsidation proteins, respectively. Several different versions of AAV packaging genes can be provided (including rep-cap cassettes and separate rep and/or cap cassettes in which the rep and/or cap genes can be left under the control of the native promoters or operably linked to heterologous promoters. Such AAV packaging genes can be introduced either transiently or stably into the host packaging cell, as is known in the art and described in more detail below.

1. rAAV Vector

A subject rAAV virion, including the targeting sequences and selectable marker(s), can be produced using standard methodology, known to those of skill in the art. The methods generally involve: (1) introducing a subject rAAV vector into a host cell; (2) introducing an AAV helper construct into the host cell, where the helper construct includes AAV coding regions capable of being expressed in the host cell to complement AAV helper functions missing from the AAV vector, (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The rAAV vector, AAV helper construct and the helper virus or accessory function vector(s) can be introduced into the host cell, either simultaneously or serially, using standard transfection techniques.

The rAAV vector, can be constructed by directly inserting the targeting sequences and the selectable marker sequences into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173, 414 and 5,139,941; International Publication Nos. WO 92/01070 (published Jan. 23, 1992) and WO 93/03769 (published Mar. 4, 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

2. AAV Helper Functions

Host cells containing the above-described rAAV vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the rAAV vectors. Thus, AAV helper functions include one, or both of the major AAV ORFs, namely the rep and cap coding regions, or functional homologues thereof. In the context of the instant invention, the cap functions include one or more mutant capsid proteins, wherein at least one capsid protein comprises at least one mutation, as described above.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) Current Topics in Microbiol. and Immunol. 158:97-129; and Kotin, R. M. (1994) Human Gene Therapy 5:793-801. Suitable homologues of the AAV rep coding region include the human herpesvirus 6 (HHV-6) rep gene which is also known to mediate AAV-2 DNA replication (Thomson et al. (1994) Virology 204:304-311).

AAV cap proteins include VP1, VP2, and VP3, wherein at least one of VP1, VP2, and VP3 comprises at least one mutation, as described above.

AAV helper functions are introduced into the host cell by transfecting the host cell with an AAV helper construct either prior to, or concurrently with, the transfection of the rAAV vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. No. 5,139,941.

Both rAAV vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the invention include the hygromycin B resistance gene (encoding Aminoglycoside phosphotranferase (APH)) that allows selection in mammalian cells by conferring resistance to hygromycin; the neomycin phosphotranferase gene (encoding neomycin phosphotransferase) that allows selection in mammalian cells by conferring resistance to G418; and the like. Other suitable markers are known to those of skill in the art.

3. AAV Accessory Functions

The host cell (or packaging cell) must also be rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

Particularly, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) J. Virol. 40:241-247; McPherson et al. (1985) Virology 147:217-222; Schlehofer et al. (1986) Virology 152:110-117.

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon, cosmid, or another virus. Accessory vectors can also be in the form of one or more linearized DNA or RNA fragments which, when associated with the appropriate control elements and enzymes, can be transcribed or expressed in a host cell to provide accessory functions.

Nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in CRC Handbook of Parvoviruses, vol. I (P. Tijssen, ed.), and Muzyczka, N. (1992) Curr. Topics. Microbiol. and Immun. 158:97-129. Specifically, early adenoviral gene regions E1a, E2a, E4, VAI RNA and, possibly, E1b are thought to participate in the accessory process. Janik et al. (1981) Proc. Natl. Acad. Sci. USA 78:1925-1929. Herpesvirus-derived accessory functions have been described. See, e.g., Young et al. (1979) Prog. Med. Virol. 25:113. Vaccinia virus-derived accessory functions have also been described. See, e.g., Carter, B. J. (1990), supra., Schlehofer et al. (1986) Virology 152:110-117.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest, e.g., the heterologous nucleic acid) from the rAAV vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions are then ready for use for genetically modifying a parent, HLA heterozygous, cell.

Therapeutic Methods

As noted above, a subject HLA homozygous cell or progeny thereof is suitable for use in a wide variety of clinical applications. As such, the present invention provides methods of treating various disorders, generally involving administering to an individual in need thereof an effective number of subject HLA homozygous cells, or progeny thereof.

A subject HLA homozygous cell or progeny thereof is introduced into an individual at a site that is appropriate to the disorder being treated. Sites and modes of administration can include, e.g., implantation (e.g., of HLA homozygous cardiomyocytes) into heart muscle; intravenous infusion (e.g., of HLA homozygous HSCs or HSC lineage cells); implantation into the pancreas (e.g., of HLA homozygous pancreatic islet cells); intracranial implantation (e.g., of HLA homozygous neural cells or glial cells); and the like.

As noted above, the prospective recipient of a subject HLA homozygous cell is an individual who has two copies of an HLA locus and therefore two HLA haplotypes, where one HLA haplotype shares a substantial proportion of the alleles in the HLA haplotype of the HLA homozygous cell. A subject HLA homozygous cell is "HLA compatible" with a prospective recipient. "HLA compatible" means that some or all of the HLA alleles in the HLA haplotype of a subject HLA homozygous cell are shared by an HLA haplotype in a prospective recipient.

The individual can have an HLA haplotype that is identical to the HLA haplotype of the HLA homozygous cell; however, the individual need not have an HLA haplotype that is identical to the HLA haplotype of the HLA homozygous cell. For example, the individual can have an HLA haplotype which shares from about 30% to about 40%, from about 40% to about 50%, from about 50% to about 60%, from about 60% to about 70%, from about 70% to about 80%, or from about 80% to about 90% of the alleles present in the HLA haplotype of the HLA homozygous cell. In some instances, the individual has an HLA haplotype having A and B alleles that are identical to the HLA haplotype of the HLA homozygous cell. In some cases, the individual has an HLA haplotype having A, B, and DR alleles that are identical to the HLA haplotype of the HLA homozygous cell. In some cases, the individual has an HLA haplotype having A, B, Cw, and DR alleles that are identical to the HLA haplotype of the HLA homozygous cell. In some cases, the individual has an HLA haplotype having A, B, Cw, DR, and DQ alleles that are identical to the HLA haplotype of the HLA homozygous cell.

Where the individual has an HLA haplotype that is not identical to the HLA haplotype of the HLA homozygous cell, the individual can be treated with one or more immunosuppressive agents. However, the amount of immunosuppressive agent that is required to suppress rejection of the transplant is less than the amount of immunosuppressive agent that is required to suppress rejection of a transplant that is less well matched to the individual than a subject HLA homozygous cell.

An "effective amount" or "effective number" of HLA homozygous cells or progeny is an amount or number that, when administered to an individual in one or more doses, provides a therapeutic effect. An effective number of HLA homozygous cells or progeny thereof ranges from about $10^3$ cells to about $10^9$ cells, e.g., from about $10^3$ cells to about $10^4$ cells, from about $10^4$ cells to about $10^5$ cells, from about $10^5$ cells to about $10^6$ cells, from about $10^6$ cells to about $10^7$ cells, from about $10^7$ cells to about $10^8$ cells, or from about $10^8$ cells to about $10^9$ cells.

As an example, an effective number of HLA homozygous pancreatic islet cells is a number of such cells that are effective to reduce a blood glucose level in an individual by at least about 10%, at least about 15%, at least about 20%, at least about 25%, at least about 30%, at least about 40%, or at least about 50% when compared to the blood glucose levels in the absence of the cells. In some embodiments, effective number of HLA homozygous pancreatic islet cells is a number that is effective to reduce blood glucose levels to a normal range. Normal blood glucose levels are typically in the range of from about 70 mg/dL to about 110 mg/dL before a meal (e.g., a fasting blood glucose level); and less than 120 mg/dL 2 hours after a meal.

As another example, an effective number of HLA homozygous cardiomocytes is a number of such cells that are effective to at least partially restore cardiac function and/or to provide for an at least 10%, at least 25%, at least 50%, or more, improvement in at least one parameter of cardiac function. Cardiac function can be measured using standard methods known to those skilled in the art.

A subject HLA homozygous cell, or an undifferentiated or differentiated progeny thereof is administered in a manner that permits the cell to graft to the intended tissue site and reconstitute or regenerate the functionally deficient area. The HLA homozygous stem cell or progeny thereof used to treat a given disorder will depend in part on the diseased tissue to which function is to be restored. The following are non-limiting examples.

Where a subject HLA homozygous cell is an HLA homozygous HSC, the HLA homozygous HSC, or undifferentiated or differentiated progeny thereof, can be used in bone marrow transplantation to treat disorders such as cancer (e.g., leukemia); acquired immunodeficiency syndrome; sickle cell anemia; and various immune system disorders. An HLA homozygous HSC, or undifferentiated or differentiated progeny thereof, can be used in bone marrow transplantation to treat an individual who has undergone chemotherapeutic treatment for a cancer and who is immunocompromised as a result.

A subject HLA homozygous cell can be induced to differentiate in vitro into a cardiomyocyte, generating an HLA homozygous cardiomyocyte. An HLA homozygous cardiomyocyte is used to treat cardiac diseases including, but not limited to, myocarditis, cardiomyopathy, heart failure, damage caused by heart attacks (e.g., areas of ischemic heart tissue), hypertension, atherosclerosis, and heart valve dysfunction.

A subject HLA homozygous cell can be induced to differentiate in vitro into a neuronal cell, or a glial cell, generating an HLA homozygous neuronal cell or glial cell. An HLA homozygous neuronal cell or glial cell can be used to treat a central nervous system (CNS) disorder. For example, an HLA homozygous neuronal cell or glial cell can be used to treat Alzheimer's disease, Parkinson's disease, Huntington's disease, AIDS associated dementia, spinal cord injury, and the like.

A subject HLA homozygous cell can be induced to differentiate in vitro into a pancreatic islet cell, generating an HLA homozygous pancreatic islet cell. An HLA homozygous pancreatic islet cell can be used to treat Type 1 diabetes.

A subject HLA homozygous cell (e.g., an HLA homozygous MSC) can be induced to differentiate in vitro into a cartilage cell, generating an HLA homozygous cartilage cell.

An HLA homozygous cartilage cell can be used to treat a disease of the joints or cartilage including but not limited to cartilage tears, cartilage thinning, osteoporosis, and osteoarthritis.

A subject HLA homozygous cell can be induced to differentiate in vitro into a renal cell, generating an HLA homozygous renal cell, which can be used to treat renal failure.

Subjects Suitable for Treatment

Subjects suitable for treatment with a subject method include individuals who have been diagnosed as having a blood cell cancer (e.g., a leukemia); individuals who have been diagnosed with AIDS; individuals with sickle cell anemia; individuals with an immune disorder, e.g., an acquired immunodeficiency, a genetic immunodeficiency; individuals with Type 1 diabetes; individuals with a nervous system disorder such as Alzheimer's disease, Parkinson's disease, spinal cord injury, stroke, etc.; individuals with a liver disorder such as hepatitis, cirrhosis, a metabolic disorder affecting the liver (e.g., lysosomal storage disease); individuals with a disorder of the cartilage or bone, e.g., individuals requiring joint replacement, individuals with osteoarthritis, individuals with osteoporosis, etc.; individuals with a cardiac disorder, e.g., myocardial infarction, coronary artery disease, or other disorder resulting in ischemic cardiac tissue; individuals with renal disorders, e.g., kidney failure (e.g., individuals on kidney dialysis); individuals with skeletal muscle disorders, such as muscular dystrophy; and individuals with a lung disorder such as emphysema, pulmonary fibrosis, idiopathic pulmonary fibrosis, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Generation of Human Stem Cells Homozygous at the HLA Locus

This Example describes generation of cell lines that have only one version of the HLA locus, instead of the two versions normally present (one on each copy of chromosome 6). The cell lines generated are thus homozygous at the HLA locus. Adeno-associated virus (AAV) vectors were used to target genes near the HLA locus in stem cells and thereby tag the locus for subsequent manipulations. The HMGA1 gene was targeted initially, as it lies just centromeric to the HLA locus on chromosome 6. The targeting vector AAV2-HMGA12-HyTK is shown schematically in FIG. 1. This targeting vector is designed to introduce a HyTK gene into exon 3 of the HMGA1 locus. The HyTK gene encodes a fusion protein with a hygromycin-resistance portion (for positive selection) and a thymidine kinase portion (for negative selection).

In the first step, H1 human embryonic stem cells were infected with the AAV2-HMGA1-HyTK vector, and several hygromycin-resistant colonies were isolated. Based on Southern blot analysis, 4 of 4 lines analyzed contained a single targeted locus.

Figure 2:
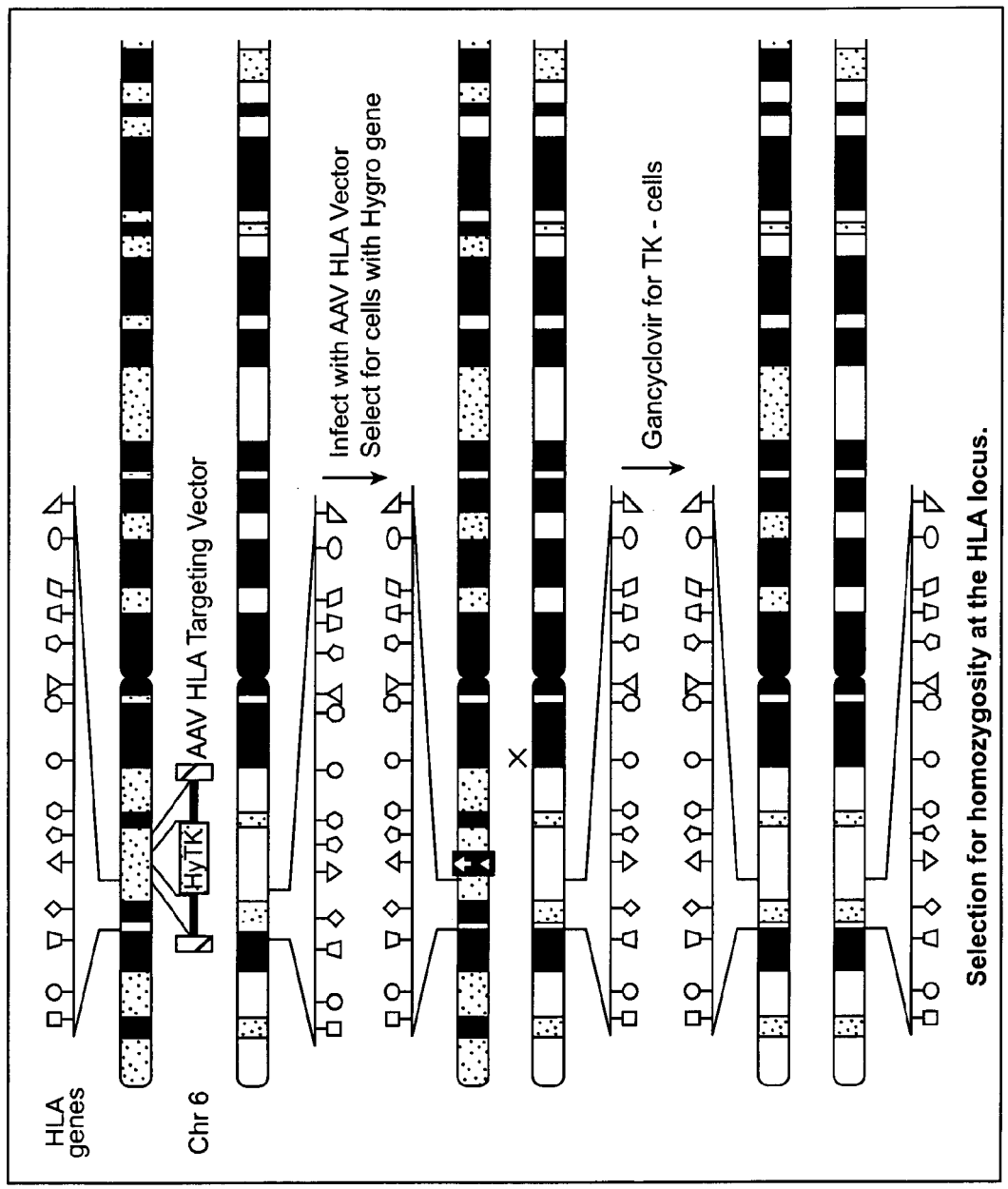
FIG. 2 is a schematic depiction of selection for homozygosity at the HLA locus.

In the second step, the lines generated in the first step were selected for loss of the HyTK transgene. Loss of the HyTK transgene could occur by homologous recombination between the 2 copies of chromosome 6, with a crossover occurring in a region centromeric to the HyTK transgene, resulting in a duplication of everything distal to the crossover. Such a recombination event should produce a cell with 2 copies of the HLA locus originally present on the untargeted chromosome, as depicted schematically in FIG. 2. Cells that were targeted at the HMGA1 locus were selected with gancyclovir for loss of the HyTK transgene. TK⁻ cells are gancyclovir resistant. One of three colonies analyzed had lost the HyTK transgene based on Southern blot analysis.

The Parental H1 human embryonic stem cells and the gancyclovir-resistant clone that lost the HyTK transgene were HLA typed. The original H1 line had two different sets of HLA alleles: A02,03; B08,35; Cw07,04; DRB03,01; and DQ02,05. The gancyclovir-resistant clone had only one set of HLA alleles (i.e., one HLA haplotype), presumably in duplicate: A02; B08; Cw07; DRB03; DQ02. This cell line would therefore be a histocompatible donor cell for any recipient with one copy of the A02-B08-Cw07-DRB03-DQ02 haplotype.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated human stem cell or a progeny thereof, wherein the stem cell or progeny thereof is homozygous for a human leukocyte antigen (HLA) haplotype, the HLA haplotype comprising an entire HLA locus; and wherein at least about 90% of the non-HLA loci in the cell or progeny thereof are heterozygous and the cell is not a parthenogenic stem cell.

2. The isolated human stem cell or progeny thereof of claim 1, wherein said cell is selected from an embryonic stem cell, a neural stem cell, a mesenchymal stem cell, a hematopoietic stem cell, and a differentiated cell.

3. The isolated human stem cell or progeny thereof of claim 1, wherein the HLA haplotype comprises alleles found in a common HLA haplotype present in a selected human population.

4. A differentiated progeny cell of the isolated human stem cell of claim 1, wherein the cell is selected from a neural cell, a glial cell, a pancreatic islet cell, a cardiomyocyte, a mesenchymal lineage cell, and a hematopoietic stem cell lineage cell.

5. A composition comprising the isolated human stem cell or progeny thereof of claim 1.

6. A composition comprising the differentiated progeny cell of claim 4.

7. The composition of claim 6, wherein the differentiated progeny cell is associated with a matrix.

8. The composition of claim 6, wherein the differentiated progeny cell is present in a tissue sheet.

9. The isolated human stem cell or progeny thereof of claim 1, wherein the stem cell or progeny thereof is homozygous for all non-HLA loci present on the short-arm of chromosome 6 that are distal to both the chromosome's centromere and said entire HLA locus.

\* \* \* \* \*